(12) United States Patent
Christensen et al.

(10) Patent No.: US 6,544,798 B1
(45) Date of Patent: Apr. 8, 2003

(54) REMOVAL OF EMBEDDING MEDIA FROM BIOLOGICAL SAMPLES AND CELL CONDITIONING ON AUTOMATED STAINING INSTRUMENTS

(75) Inventors: Kimberly Christensen, Tucson, AZ (US); Ethel R. Macrea, Tucson, AZ (US); Noemi Sebastiao, Oro Valley, AZ (US); Glen Ward, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/853,200

(22) Filed: May 11, 2001

Related U.S. Application Data

(63) Continuation-in-part of application No. 09/721,096, filed on Nov. 20, 2000, which is a continuation of application No. PCT/US99/20353, filed on Sep. 3, 1999.

(30) Foreign Application Priority Data

Feb. 26, 1999 (US) ............................................. 99/04181
Sep. 3, 1999 (US) ............................................. 99/20353

(51) Int. Cl.⁷ ................................................ G01N 1/18
(52) U.S. Cl. ........................ 436/177; 436/17; 436/175; 435/40.5; 435/40.52
(58) Field of Search ................................ 436/8, 17, 18, 436/63, 175, 177; 435/40.5, 40.51, 40.52, 962

(56) References Cited

U.S. PATENT DOCUMENTS

| | | |
|---|---|---|
| 4,043,292 A | 8/1977 | Rogers et al. |
| 4,384,193 A | 5/1983 | Kledzik et al. |
| 4,543,236 A | 9/1985 | von Gise |
| 4,629,862 A | 12/1986 | Kitagawa et al. |
| 4,644,807 A | 2/1987 | Mar |
| 4,746,491 A | 5/1988 | Ohlin |
| 4,858,155 A | 8/1989 | Okawa et al. |
| 4,865,986 A | 9/1989 | Coy et al. |
| 4,888,998 A | 12/1989 | Buzza et al. |
| 5,023,187 A | 6/1991 | Koebler et al. |

(List continued on next page.)

FOREIGN PATENT DOCUMENTS

| | | | |
|---|---|---|---|
| WO | 93/09486 | | 5/1993 |
| WO | 95/24498 | * | 9/1995 |
| WO | 99/44030 | * | 9/1999 |
| WO | 00/14507 | | 3/2000 |
| WO | 01/73399 | | 10/2001 |
| WO | 01/88500 | * | 11/2001 |
| WO | 02/23156 | * | 3/2002 |

OTHER PUBLICATIONS

Bankfalvi, A. et al. (1994) "Wet autoclaving pretreatment for antigen retrieval in diagnostic immunohistochemistry." *Journal of Pathology* 174: 223–228.

(List continued on next page.)

*Primary Examiner*—Maureen M. Wallenhorst
(74) *Attorney, Agent, or Firm*—McDonnell Boehnen Hulbert & Berghoff

(57) ABSTRACT

The present invention provides reagents for use in an automated environment for cell conditioning of biological samples wherein the cells or tissues are predisposed for access by reagent molecules for histochemical and cytochemical staining procedures. The reagents include components optimized to facilitate molecular access to cells and cell constituents within the biological sample. The present invention also provides reagents for use in an automated environment for removing or etching embedding media by exposing a biological sample to be stained in histochemical or cytochemical procedures without the dependence on organic solvents. The reagents include components optimized to facilitate removal or etching of the embedding media from the biological sample.

16 Claims, 9 Drawing Sheets

U.S. PATENT DOCUMENTS

| | | | |
|---|---|---|---|
| 5,075,079 A | | 12/1991 | Kerr et al. |
| 5,244,787 A | * | 9/1993 | Key et al. .................... 435/7.2 |
| 5,273,905 A | | 12/1993 | Muller et al. |
| 5,417,123 A | | 5/1995 | D'Autry |
| 5,578,452 A | * | 11/1996 | Shi et al. ................. 435/40.52 |
| 5,595,707 A | * | 1/1997 | Copeland et al. ............. 422/63 |
| 5,601,141 A | | 2/1997 | Gordon et al. |
| 5,614,376 A | | 3/1997 | Copley et al. |
| 5,645,114 A | | 7/1997 | Bogen et al. |
| 5,672,696 A | * | 9/1997 | Wang et al. ................ 536/25.4 |
| 6,296,809 B1 | * | 10/2001 | Richards et al. ............ 141/145 |

OTHER PUBLICATIONS

Fox, C.H. et al. (1985) "Formaldehyde fixation." *Journal of Histochemistry and Cytochemistry* 33 (8): 845–853.

Kawai, K. et al. (1994) "Heat–induced antigen retrieval of proliferating cell nuclear antigen and p53 protein in formalin–fixed, paraffin–embedded sections." *Pathology International* 44: 759–764.

Mason, J.T. & O'Leary, T.J. (1991) "Effects of formaldehyde fixation on protein secondary structure: a calorimetric and infrared spectroscopy investigation." *Journal of Histochemistry and Cytochemistry* 39 (2): 225–229.

MaWhinny, W.H.B. et al. (1990) "Automated immunohistochemistry." *Journal of Clinical Pathology* 43: 591–596.

McNicol, A.M. & Richmond, J.A. (1998) "Optimizing immunohistochemistry: antigen retrieval and signal amplification." *Histopathology* 32: 97–103.

Miller, R.T. & Estran, C. (1995) "Heat–induced epitope retrieval with a pressure cooker." *Applied Immunohistochemistry* 3 (3): 190–193.

Morgan, J.M. et al. (1994) "Possible role of tissue–bound calcium ions in citrate–mediated high–temperature antigen retrieval." *Journal of Pathology* 174: 301–307.

Norton, A.J. et al. (1994) "Brief, high–temperature heat denaturation (pressure cooking): a simple and effective method of antigen retrieval for routinely processed tissues." *Journal of Pathology* 173: 371–379.

Pasha, T. et al. (1995) "Nuclear antigen retrieval utilizing steam heat." *Laboratory Investigations* 72: 167A, abstract#979.

Pertschuk, L.P. et al. (1994) "Estrogen receptor immunocytochemistry: the promise and the perils." *Journal of Cellular Biochemistry* suppl. 19: 134–137.

Pons, C. et al. (1995) "Antigen retrieval by wet autoclaving for p53 immunostaining." *Applied Immunohistochemistry* 3(4): 265–267.

Shi, S.–R. et al. (1997) "Antigen retrieval immunohistochemistry: past, present, and future." *Journal of Histochemistry and Cytochemistry* 45 (3): 327–343.

Sibony, M. et al. (1995) "Methods in laboratory investigation: Enhancement of mRNA in situ hybridization signal by microwave heating." *Laboratory Investigation* 73 (4): 586–591.

Sperry, A. et al. (1996) "Microwave treatment enhances detection of RNA and DNA by in situ hybridization." *Diagnostic Molecular Pathology* 5(4): 291–296.

Stark, E. et al. (1988) "An automated device for immunohistochemistry." *Journal of Immunological Methods* 107: 89–92.

Stross, W.P. et al. (1989) "Automation of APAAP immunocytochemical technique." *Journal of Clinical Pathology* 42: 106–112.

Taylor, C.R. et al. (1995) "A comparative study of antigen retrieval heating methods." *CAP Today* 9: 16–22.

International Search Report for application PCT/US99/20353.

International Search Report for application PCT/US99/04379.

International Search Report for application PCT/US99/04181.

\* cited by examiner

REMOVAL OF EMBEDDING MEDIA FROM BIOLOGICAL SAMPLES AND CELL CONDITIONING ON AUTOMATED STAINING INSTRUMENTS

REFERENCE TO RELATED APPLICATIONS

This application is a continuation-in-part of U.S. application Ser. No. 09/721,096, filed Nov. 22, 2000, U.S. application Ser. No. 09/721,096 claimed the benefit of priority from International Application No. PCT/US99/20353, filed Sep. 3, 1999, which was published on Mar. 16, 2000 as WO 00/14507. International Application No. PCT/US99/20353, in turn, claimed the benefit of priority from U.S. Provisional Patent Application Ser. No. 60/099,018, filed Sep. 3, 1998; which is a continuation of U.S. patent application Ser. No. 09/259,240, filed Feb. 26, 1999, now U.S. Pat. No. 6,296,809; and International Application No. PCT/US99/04181, filed Feb. 26, 1999, which was published on Sep. 2, 1999 as WO 99/44030. U.S. patent application Ser. No. 09/721,096, filed Nov. 22, 2000; International Patent Application No. PCT/US99/20353, filed Sep. 3, 1999, and published as WO 00/14507 on Mar. 16, 2000; U.S. Provisional App. Ser. No. 60/099,018, filed Sep. 3, 1998; U.S. patent application Ser. No. 09/259,240, filed Feb. 26, 1999, now U.S. Pat. No. 6,296,809 and International Patent App. No. PCT/US99/04181, filed Feb. 26, 1999, and published as WO 99/44030 on Sep. 2, 1999, are all hereby incorporated by reference.

BACKGROUND OF THE INVENTION

1. Field of the Invention

The present invention relates to solutions methods, and instruments for conditioning cells or tissues so as to increase the accessibility of various molecules to their respective targets and generally to improve tissue and cell readability of biological samples on automated instruments prior to immunohistochemical (IHC), in situ hybridization (ISH) or other histochemical or cytochemical manipulations.

2. Summary of the Related Art

All patents, patent applications and non-patent articles or references mentioned herein are hereby incorporated by reference to the extent that they are not contradictory.

The diagnosis of disease based on the interpretation of tissue or cell samples taken from a diseased organism has expanded dramatically over the past few years. In addition to traditional histological staining techniques and immunohistochemical assays, in situ techniques such as in situ hybridization and in situ polymerase chain reaction are now used to help diagnose disease states in humans. Thus, there are a variety of techniques that can assess not only cell morphology, but also the presence of specific macromolecules within cells and tissues. Each of these techniques requires that sample cells or tissues undergo preparatory procedures that may include fixing the sample with chemicals such as an aldehyde (such as formaldehyde, glutaraldehyde), formalin substitutes, alcohol (such as ethanol, methanol, isopropanol) or embedding the sample in inert materials such as paraffin, celloidin, agars, polymers, resins, cryogenic media or a variety of plastic embedding media (such as epoxy resins and acrylics). Other sample tissue or cell preparations require physical manipulation such as freezing (frozen tissue section) or aspiration through a fine needle (fine needle aspiration (FNA)). Regardless of the tissue or cell sample or its method of preparation or preservation, the goal of the technologist is to obtain accurate, readable and reproducible results that permit the accurate interpretation of the data. One way to provide accurate, readable and reproducible data is to prepare the tissue or cells in a fashion that optimizes the results of the test regardless of the technique employed. In the case of immunohistochemistry and in situ techniques this means increasing the amount of signal obtained from the specific probe (e.g., antibody, DNA, RNA, etc.). In the case of histochemical staining it may mean increasing the intensity of the stain or increasing staining contrast.

Without preservation, tissue samples rapidly deteriorate such that their use in diagnostics is compromised shortly after removal from their host. In 1893, Ferdinand Blum discovered that formaldehyde could be used to preserve or fix tissue so that it could be used in histochemical procedures. The exact mechanisms by which formaldehyde acts in fixing tissues are not fully established, but they involve cross-linking of reactive sites within the same protein and between different proteins via methylene bridges (Fox et al., J. Histochem. Cytochem. 33: 845–853 (1985)). Recent evidence suggests that calcium ions also play a role (Morgan et al., J. Path. 174: 301–307 (1994)). These links cause changes in the quaternary and tertiary structures of proteins, but the primary and secondary structures appear to be preserved (Mason et al., J. Histochem. Cytochem. 39: 225–229 (1991)). The extent to which the cross-linking reaction occurs depends on conditions such as the concentration of formalin, pH, temperature and length of fixation (Fox et al., J. Histochem. Cytochem. 33: 845–853 (1985)). Some antigens, such as gastrin, somatostatin and iantitrypsin, may be detected after formalin fixation, but for many antigens, such as intermediate filaments and leukocyte markers, immunodetection after formalin treatment is lost or markedly reduced (McNicol & Richmond, Histopathology 32: 97–103 (1998)). Loss of antigen immunoreactivity is most noticeable at antigen epitopes that are discontinuous, i.e. amino acid sequences where the formation of the epitope depends on the confluence of portions of the protein sequence that are not contiguous.

Antigen retrieval refers to the attempt to "undo" the structural changes that treatment of tissue with a cross-linking agent induces in the antigens resident within that tissue. Although there are several theories that attempt to describe the mechanism of antigen retrieval (e.g., loosening or breaking of crosslinkages formed by formalin fixation), it is clear that modification of protein structure by formalin is reversible under conditions such as high-temperature heating. It is also clear that several factors affect antigen retrieval: heating, pH, molarity and metal ions in solution (Shi et al., J. Histochem. Cytochem. 45: 327–343 (1997)).

Microwave heating appears to be the most important factor for retrieval of antigens masked by formalin fixation. Microwave heating (100±5° C.) generally yields better results in antigen retrieval immunohistochemistry (AR-IHC).

Different heating methods have been described for antigen retrieval in IHC such as autoclaving (Pons et al, Appl. Immunohistochem. 3: 265–267 (1995); Bankfalvi et al., J. Path. 174: 223–228 (1994)); pressure cooking (Miller & Estran, Appl. Immunohistochem. 3: 190–193 (1995); Norton et al., J. Path. 173: 371–379 (1994)); water bath (Kawai et al., Path. Int. 44: 759–764 (1994)); microwaving plus plastic pressure cooking (U.S. Pat. No. 5,244,787; Pertschuk et al., J. Cell Biochem. 19(suppl.): 134–137 (1994)); and steam heating (Pasha et al., Lab. Invest. 72: 167A (1995); Taylor et al., CAP Today 9: 16–22 (1995)).

Although some antigens yield satisfactory results when microwave heating is performed in distilled water, many antigens require the use of buffers during the heating process. Some antigens have particular pH requirements such that adequate results will only be achieved in a narrow pH range. Presently, most antigen retrieval solutions are used at a pH of approximately 6–8, but there is some indication that slightly more basic solutions may provide marginally superior results (Shi, et al., J. Histochem. Cytochem. 45: 327–343 (1997)).

Although the chemical components of the antigen retrieval solution, including metal ions, may play a role as possible co-factors in the microwave heating procedure, thus far, no single chemical has been identified that is both essential and best for antigen retrieval.

Many solutions and methods are used routinely for staining enhancements. These may include but are not limited to distilled water, EDTA, urea, Tris, glycine, saline and citrate buffer. Solutions containing a variety of detergents (ionic or non-ionic surfactants) may also facilitate staining enhancement under a wide range of temperatures (from ambient to in excess of 100° C.).

In addition to cell surface molecules that may be present on the exterior portion of the cell, other molecules of interest in IHC, ISH and other histochemical and cytochemical manipulations are located within the cell, often on the nuclear envelope. Some of these molecules undergo molecular transformation when exposed to a fixative (coagulative or precipitive) such as formalin. Thus with respect to these molecules it is desirable to not only overcome the effects of fixation but also to increase the permeability of the cell in order to facilitate the interaction of organic and inorganic compounds with the cell.

Other tissue samples may not have been subjected to cross-linking agents prior to testing, but improved results with respect to these tissues is also important. There are a variety of non-formalin methods for preserving and preparing cytological and histological samples. Examples of these methods include, but are not limited to: a) hematology smears, cytospins™, ThinPreps™, touch preps, cell lines, Ficoll separations, etc. are routinely preserved in many ways which includes but are not limited to, air-drying, alcoholic fixation, spray fixatives and storage mediums such as sucrose/glycerin; b) tissues and cells (either fixed or unfixed) may be frozen and subsequently subjected to various stabilizing techniques which include, but are not limited to, preservation, fixation and desiccation; c) tissues and cells may be stabilized in a number of non-cross-linking aldehyde fixatives, non-aldehyde containing fixatives, alcoholic fixatives, oxidizing agents, heavy metal fixatives, organic acids and transport media.

One way to improve testing results is to increase the signal obtained from a given sample. In a general sense, increased signal can be obtained by increasing the accessibility of a given molecule for its target. As in the case for antigens found within the cell, targets within the cell can be made more accessible by increasing the permeability of the cell thereby permitting a greater number of molecules entry into the cell, thereby increasing the probability that the molecule will "find" its target. Such increased permeability is especially important for techniques such as ISH, in situ PCR, IHC, histochemistry and cytochemistry.

Tissues and cells are also embedded in a variety of inert media (paraffin, celloidin, OCT™, agar, plastics or acrylics etc.) to help preserve them for future analysis. Many of these inert materials are hydrophobic and the reagents used for histological and cytological applications are predominantly hydrophilic; therefore, the inert medium may need to be removed from the biological sample prior to testing. For example, paraffin embedded tissues sections are prepared for subsequent testing by removal of the paraffin from the tissue section by passing the slide through various organic solvents such as toluene, xylene, limonene or other suitable solvents. These organic solvents are very volatile causing a variety of problems including requiring special processing (e.g., deparaffinization is performed in ventilated hoods) and requires special waste disposal. The use of these organic solvents increases the cost of analysis and exposure risk associated with each tissue sample tested and has serious negative effects for the environment.

Presently, there is no available technique for removing inert media from sample tissue by directly heating the slide in an automated fashion. Neither is it currently possible to remove inert media from sample tissue while conditioning the sample tissue or cell in a one-step automated staining process.

The methods of the present invention permit a) automated removal of embedding media without the use of organic solvents, thus exposing the cells for staining and thereby reducing time, cost and safety hazards, b) automated cell conditioning without automated removal of embedding media from the sample cell or tissue, c) a multi-step automated process that exposes the cells, performs cell conditioning and increases permeability of the cytological or histological specimens, thereby increasing sample readability and improving interpretation of test data. The methods of the present invention can be used for improving the stainability and readability of most histological and cytological samples used in conjunction with cytological and histological staining techniques.

SUMMARY OF THE INVENTION

The present invention relates to solutions, methods and instruments for cell or tissue conditioning, which improves the accessibility of molecules in biological samples during histochemical or cytochemical assays. The conditioning may be performed at any point in a histochemical or cytochemical protocol.

The present invention further relates to an automated method for exposing biological samples for use in histological or cytological testing procedures by removing the embedding media without the use of organic solvents.

The present invention also relates to an automated method for the simultaneous exposing and cell conditioning of biological samples for histochemical and cytochemical applications.

DETAILED DESCRIPTION OF THE PREFERRED EMBODIMENTS

One embodiment of the present invention relates to the exposing of biological samples by removal of the inert materials in which biological samples have been embedded for preservation and support. In a preferred embodiment of the present invention, paraffin or other inert materials are removed from biological samples by heating one side of the biological sample. This may be accomplished by contact heating of the microscope slide on which the embedded biological samples have been placed. Other inert materials that can be removed from embedded biological samples include but are not limited to agars and cryogenic media. This process of removal of inert embedding media or etching of embedding media is referred to herein as exposing.

In a preferred method of the present invention, the paraffin-embedded biological sample laying on the glass slide is first heated by a heating element. The heating element exposes heat on one side of the biological sample (such as the thermal platforms disclosed in U.S. patent application Ser. No. 09/259,240, now U.S. Pat. No. 6,296, 809 herein incorporated by reference) within an automated staining instrument (U.S. patent application Ser. No. 08/995, 052 filed on Dec. 19, 1997, now U.S. Pat. No. 6,045,759 and U.S. provisional patent application Ser. No. 60/076,198 filed on Feb. 27, 1998, both of which are herein incorporated by reference) such that the sample slide is dried and the paraffin is melted.

Heating Elements

Figure 1:
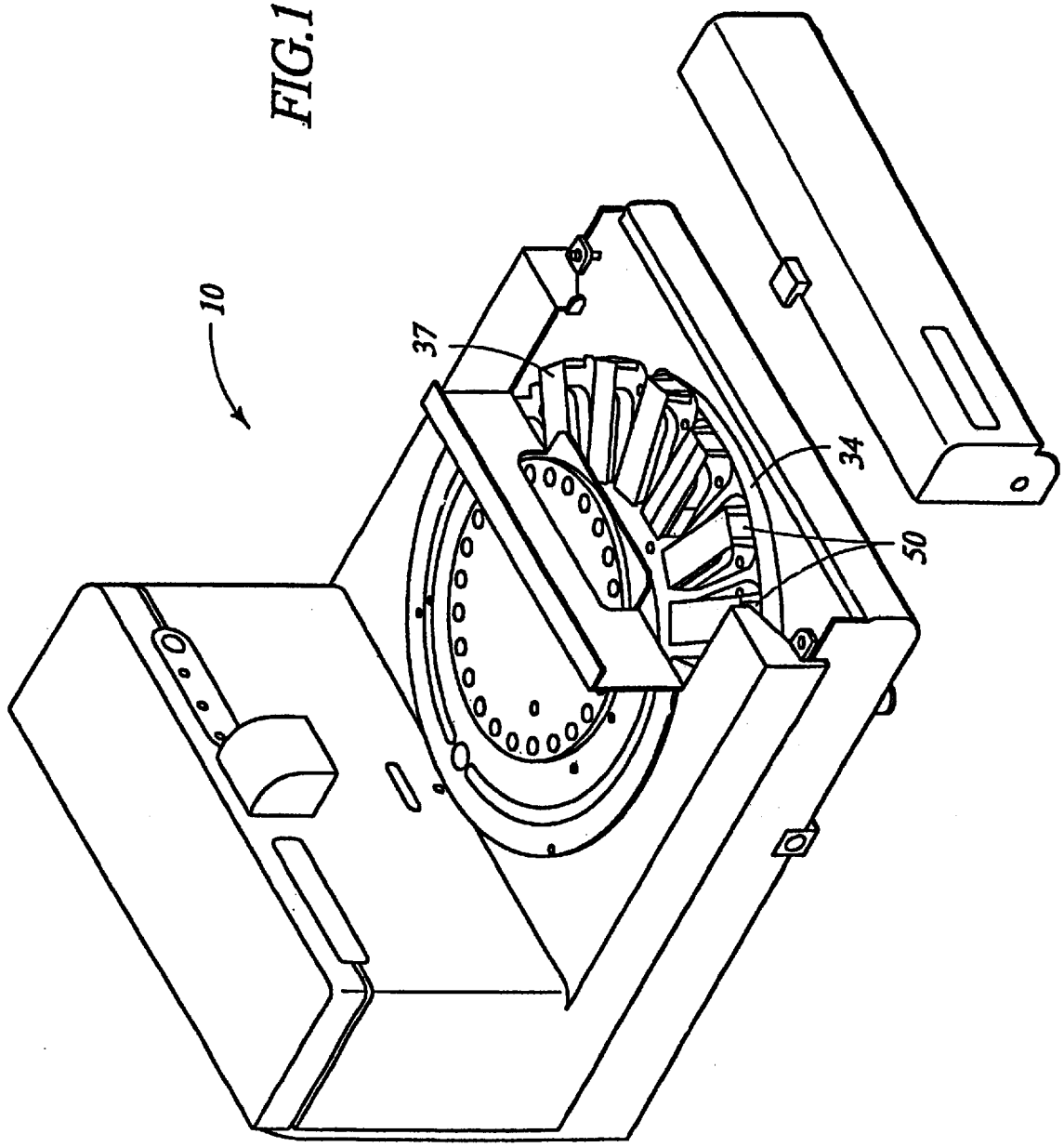
FIG. 1 is a perspective view of the present invention shown with the slide hood open and the carousel door removed.

As discussed in U.S. patent application Ser. No. 09/259, 240, now U.S. Pat. No. 6,296,809 (which is incorporated by reference) and referring now in detail to the drawings wherein like parts are designated by like reference numerals throughout, there is illustrated in FIG. 1 a perspective view of the molecular pathology apparatus according to the present invention which is designated generally by reference numeral 10. Apparatus 10 is designed to automatically stain or otherwise treat tissue mounted on microscope slides with nucleic acid probes, antibodies, and/or reagents associated therewith in the desired sequence, time and temperature. Tissue sections so stained or treated are then to be viewed under a microscope by a medical practitioner who reads the slide for purposes of patient diagnosis, prognosis, or treatment selection.

Figure 2:
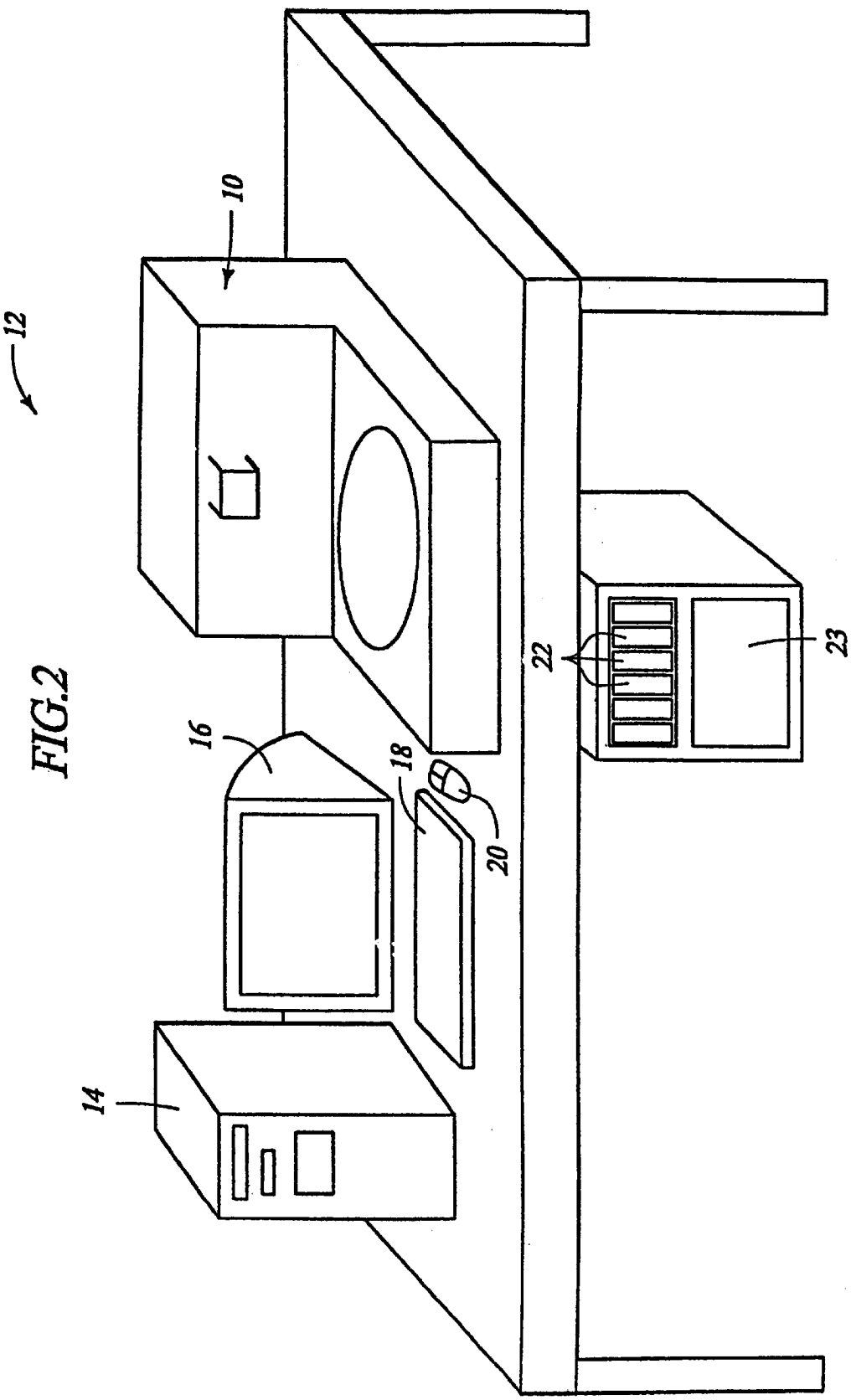
FIG. 2 is a perspective view of the present invention shown in conjunction with a computer and other instruments with which it operates.

In a preferred embodiment, apparatus 10 functions as one component or module of a system 12 (FIG. 2) which also comprises a host computer 14 preferably a personal computer, monitor 16, keyboard 18, mouse 20, bulk fluid containers 22, waste container 23 and related equipment. Additional staining modules or other instruments may be added to system 12 to form a network with computer 14 functioning as a server. Alternatively, some or all of these separate components could be incorporated into apparatus 10 making it a stand-alone instrument.

The preferred configuration of apparatus 10 as well as system 12 is generally as described in U.S. patent application Ser. No. 08/995,052 filed Dec. 19, 1997, now U.S. Pat. No. 6,045,759 as well as in the Ventana NexES User's Guide available from Ventana Medical Systems, Inc. (Tuscon, Ariz.), both incorporated herein, except with respect to the novel heating system, slide support, bulk fluids module, volume adjust, and slide wipe as disclosed below. For purposes of clarity, detailed descriptions of those components found in both the present invention and the incorporated references are omitted.

In brief, apparatus 10 is a microprocessor controlled staining instrument that automatically applies chemical and biological reagents to tissue mounted on standard glass microscope slides. A carousel supporting radially positioned glass slides is revolved by a stepper motor to place each slide under one of a series of reagent dispensers. Apparatus 10 controls dispensing, washing, mixing, and heating to optimize reaction kinetics. The computer controlled automation permits use of apparatus 10 in a walk-away manner, i.e. with little manual labor.

Figure 3:
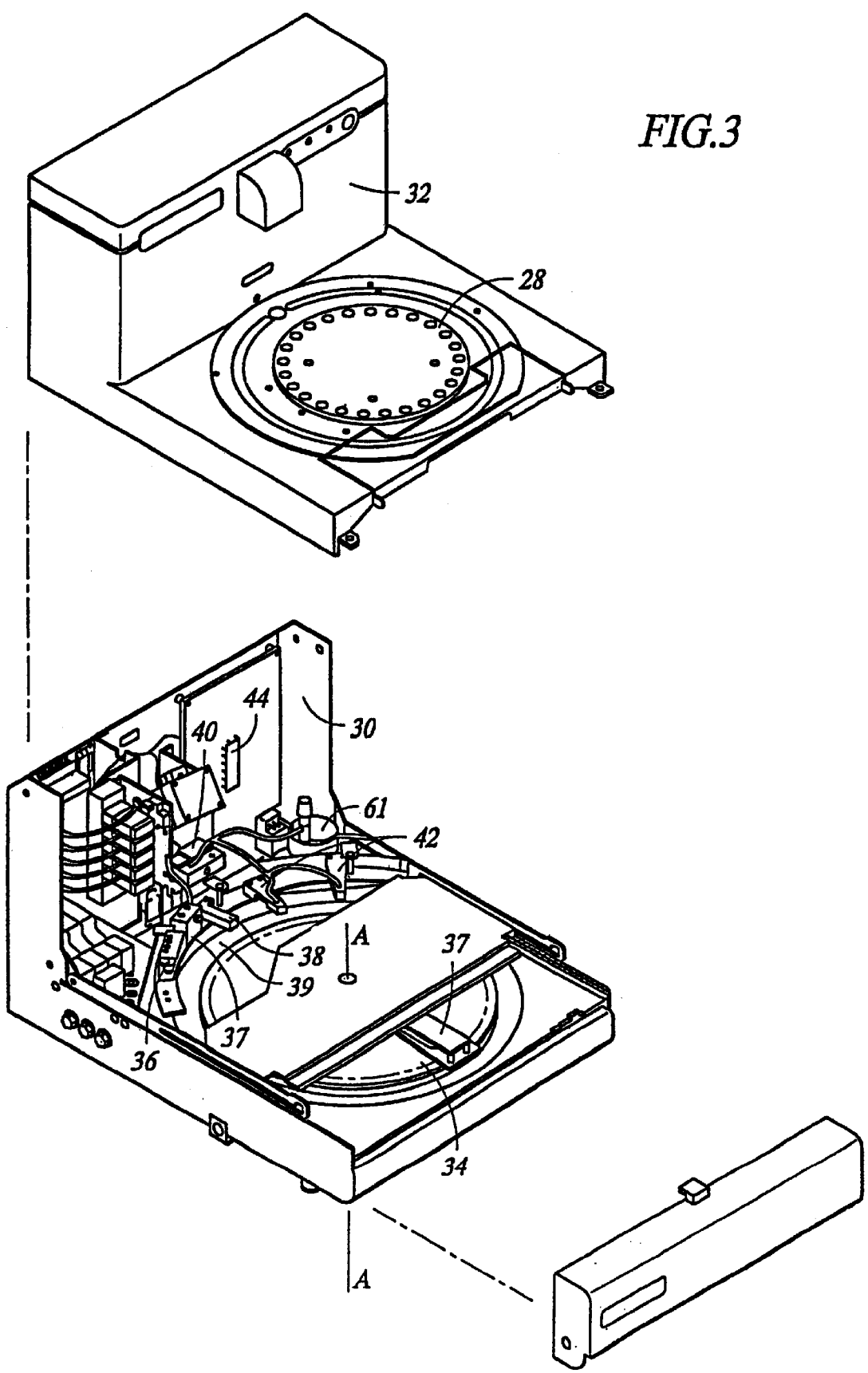
FIG. 3 is an exploded view of the present invention.

More particularly, apparatus 10 comprises a housing formed of a lower section 30 removably mounted or hinged to an upper section 32. A slide carousel 34 is mounted within lower section 30 for rotation about axis A—A. As set forth in greater detail below, a plurality of thermal platforms 50 are mounted radially about the perimeter of carousel 34 upon which standard glass slides with tissue samples may be placed. Carousel 34 is preferably constructed of stainless steel. It is a key feature of the present invention that the temperature of each slide may be individually controlled by means of various sensors and microprocessors as described herein. Also housed within apparatus 10 (FIG. 3) are wash dispense nozzles 36, Coverslip™ dispense nozzle 37, fluid knife 38, wash volume adjust nozzle 39, bar code reader mirror 40, and air vortex mixers 42 the details of which are discussed hereinafter.

Figure 4:
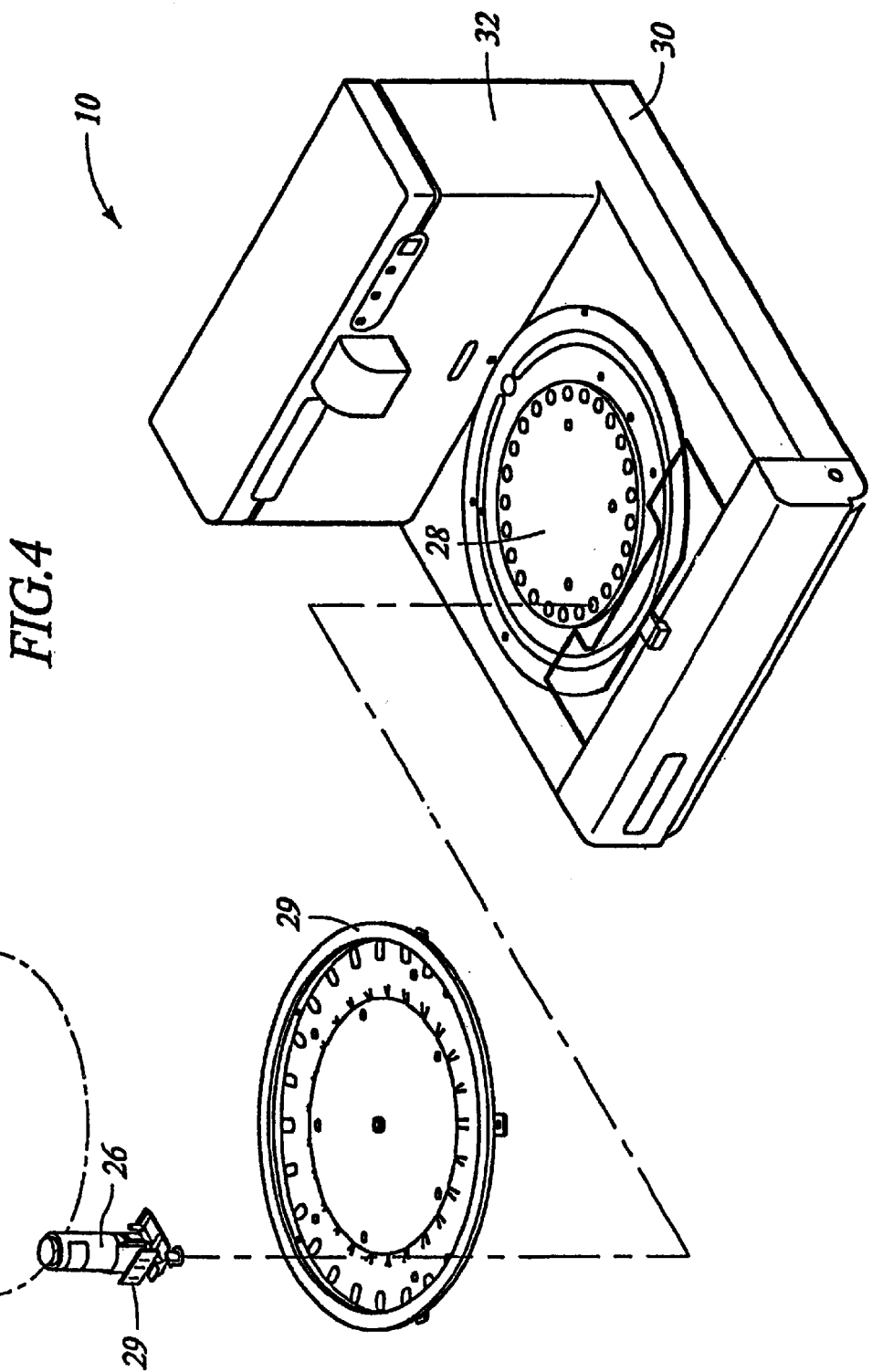
FIG. 4 is a perspective view of the present invention shown with a reagent dispenser.

Rotatably mounted atop upper section 32 is a reagent carousel 28. Dispensers 26 are removably mounted to reagent tray 29 (FIG. 4) which, in turn, is adapted to engage carousel 28. Reagents may include any chemical or biological material conventionally applied to slides including nucleic acid probes or primers, polymerase, primary and secondary antibodies, digestion enzymes, pre-fixatives, post-fixatives, blocking agents, readout chemistry, and counterstains. Reagent dispensers 26 are preferably bar code labeled 29 for identification by the computer. For each slide, a single reagent is applied and then incubated for a precise period of time in a temperature-controlled environment. Mixing of the reagents is accomplished by compressed air jets 42 aimed along the edge of the slide thus causing rotation of the reagent. After the appropriate incubation, the reagent is washed off the slide using nozzles 36. Then the remaining wash buffer volume is adjusted using the volume adjust nozzle 39. Coverslip™ solution, to inhibit evaporation, is then applied to the slide via nozzle 37. Air knife 38 divides the pool of Coverslip™ followed by the application of the next reagent. These steps are repeated as the carousels turn until the protocol is completed.

In addition to host computer 14, apparatus 10 preferably includes its own microprocessor 44 to which information from host computer 14 is downloaded. In particular, the computer downloads to microprocessor 44 both the sequence of steps in a run program and the sensor monitoring and control logic called the "run rules" as well as the temperature parameters of the protocol. Model No. DS2251T 128K from Dallas Semiconductor, Dallas Tex. is an example of a microprocessor that can perform this function.

Figure 5:
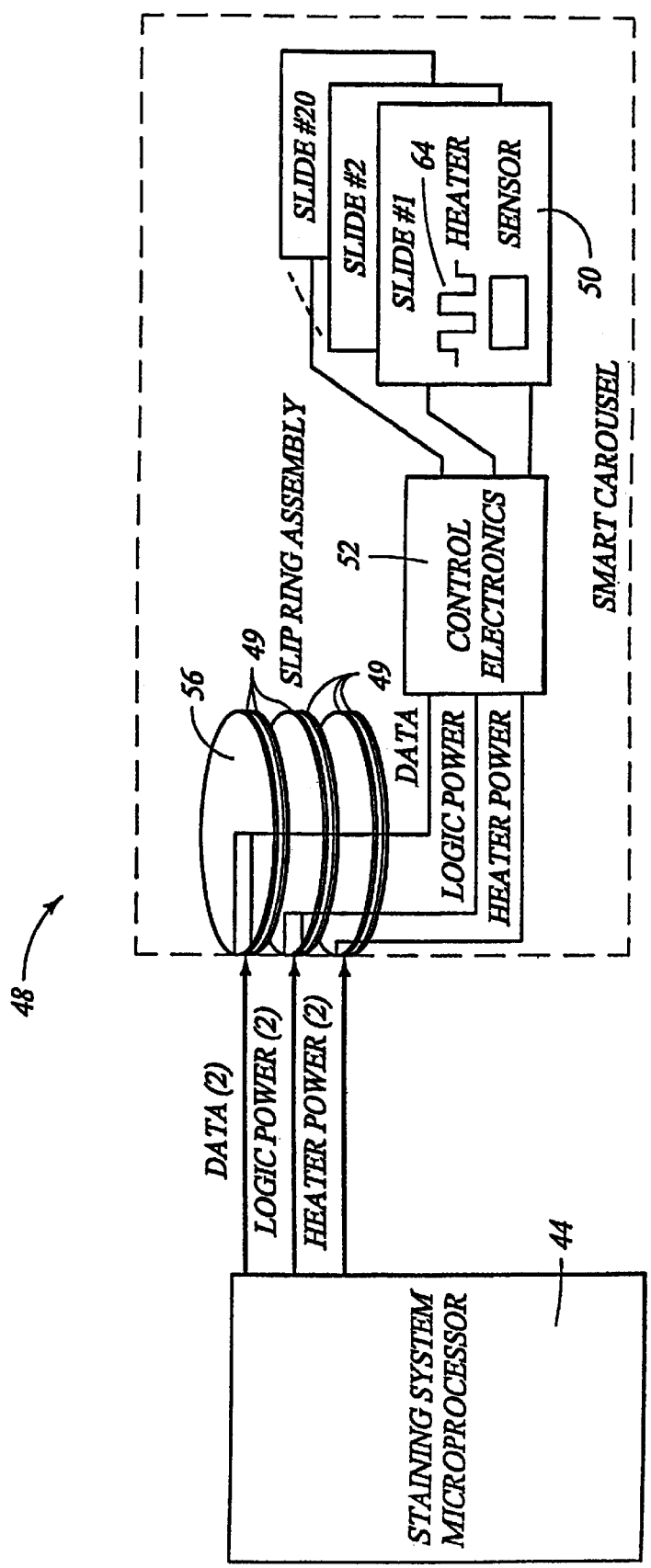
FIG. 5 is a block diagram of the heating system of the present invention.

Turning now to FIG. 5 there is shown a block diagram of the slide heating system 48. The system generally comprises about twenty thermal platforms 50, radially mounted to carousel 34, for heating the slides and monitoring the temperature thereof, and control electronics printed circuit board 52 also mounted to the slide carousel for monitoring the sensors and controlling the heaters. Control electronics 52 are mounted under the rotating slide carousel 34. Information and power are transferred from the fixed instrument platform to the rotating carousel via a slip ring assembly 56. This information includes the temperature parameters needed for heating the slides (upper and lower) communicated from microprocessor 44 (after having been downloaded from computer 14) to control electronics 52 as described below. If, during a run, the slide temperature is determined to be below the programmed lower limit, the thermal platform heats the slide. Likewise, if the slide temperature is found to be above the upper limit, heating is stopped. A power supply of sufficient capacity to provide about eight watts per heater is provided to meet the requisite rate of temperature rise (a/k/a "ramp up").

Similarly, in an alternate embodiment, the cooling of the slides may be likewise controlled, as described subsequently. In one alternate embodiment, cooling platforms are mounted below the slide. The cooling platforms may comprise Peltier-type thermal transducers. In an alternative embodiment, a cooling device such as a fan (not shown) may optionally be provided if rapid cooling of the slides is required for particular applications. The cooling device will modify the ambient air for all of the platforms, necessitating the heaters corresponding to the slides which should not be cooled to compensate for the drop in ambient air temperature. The slide heating system described herein uses conduction heating and heats slides individually. The system provides more accurate on-slide temperature and allows for temperature settings on a slide by slide basis.

Heating of the Slide

Typically, the biological sample is placed on a top surface of a slide (such as a glass slide). The slide is then placed on top of the thermal platform 50, so that the bottom surface of the slide is in contact with the thermal platform. As discussed previously, the thermal platform 50, via conduction, heats the bottom portion of the slide. After the heating of the biological sample, the inert material may be removed from the slide by a fluid (as a gas or liquid). For example, the inert material may be rinsed with de-ionized water and a surfactant.

The current method for deparaffinization is markedly different from what was performed in the prior art. Prior art methods include: (1) using organic solvents to dissolve the paraffin; or (2) manually using heat and dissolving agents to dissolve the paraffin. In contrast, in one aspect of the current invention, the deparaffinization does not involve a chemical reaction that dissolves the paraffin. In particular, the fluid which is placed on the sample does not solvate the paraffin. Instead, the current method involve the melting of the paraffin from the tissue and the washing of it away with fluids. In one embodiment, the fluid which is placed on top of the embedded sample is not miscible or capable of being mixed with the paraffin. One example of this is water, which is not miscible with paraffin. In addition, water has a higher density than liquified paraffin. The paraffin, when melted, floats to the top of the fluid so that the top of the slide may be rinsed, rinsing off of the melted paraffin.

In another method of the present invention, a paraffin embedded biological sample is placed on a glass microscope slide and the microscope slide is placed on a heating element. A reagent is placed on the biological sample slide, the biological sample slide is then exposed to elevated temperatures that will permit the melting of the inert material, and after which the inert material may be removed from the slide by a fluid (as a gas or liquid).

In a preferred embodiment of the present invention, reagents are used in conjunction with heating the embedded biological samples. Suitable reagents may include, but are not limited to, de-ionized water, citrate buffer (pH 6.0–8.0), Tris-HCl buffer (pH 6–10), phosphate buffer (pH 6.0–8.0), SSC buffer, APK Wash™, acidic buffers or solutions (pH 1–6.9), basic buffers or solutions (pH 7.1–14), mineral oil, Norpar, canola oil, and PAG oil. Each of these reagents may also contain ionic or non-ionic surfactants such as Triton X-100, Tween, Brij, saponin and sodium dodecylsulfate.

In a method of the present invention, the temperature of the heating element is raised to a temperature in excess of the melting point of the inert material. For example, the melting point of pure paraffin is listed as 50–57° C. in the Merck index. Thus, in the method of the present invention, the temperature is in excess of the melting point of the paraffin in which the biological sample is embedded. In a preferred method of the present invention, the temperature is raised in excess of 50° C. to about 130° C.

In a method of the present invention, the duration of time required to melt the inert material will vary according to the temperature used and the embedding material. Typically, in an automated system, a processor, such as a microprocessor, is used in conjunction with a memory. The amount of time and the temperature required to melt the paraffin is contained within a table contained in the memory.

The paraffin embedded biological sample is subjected to elevated temperatures ranging from 5 minutes to 60 minutes. The heating element used in the method of the present invention requires that sufficient contact be maintained between the surface on which the biological sample is placed and the heating element.

Figure 6:
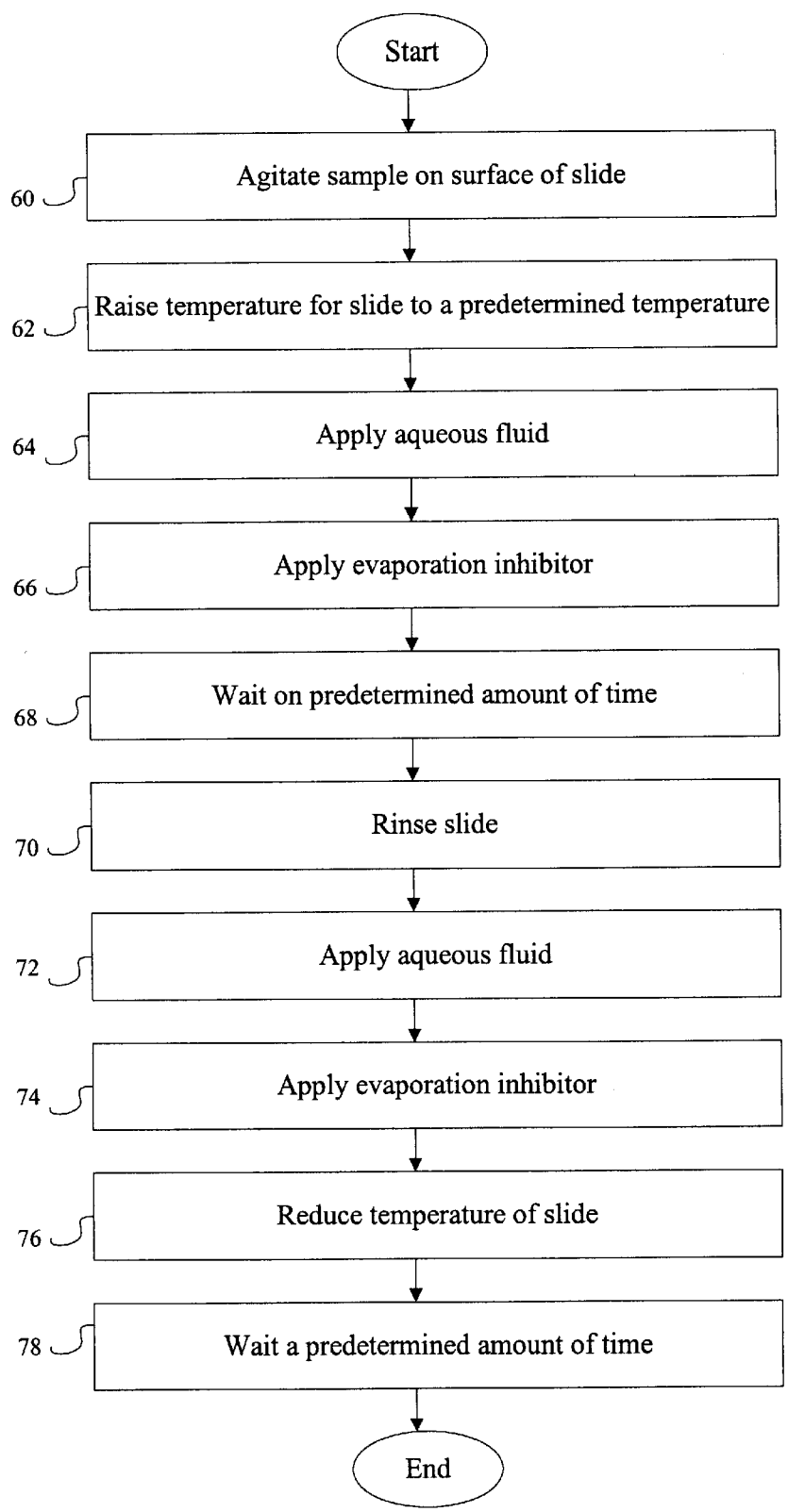
FIG. 6 is a flow chart for one embodiment for removing the embedding media from a slide.

Referring to FIG. 6, there is shown a flow chart for one embodiment for removing the embedding media from a slide. As shown at block 60, the surface of the slide is agitated. In one embodiment, the vortex air mixers 42 are used to stir the biological sample on the surface of the slide. As shown at block 62, the temperature for the slide is raised to a predetermined temperature. In one embodiment, the temperature of the slides is raised by heating using the thermal platforms 50. As one example for in situ hybridization (ISH), the initial heating step heats the slide to 65° C. for 16 minutes and then to 75° C. for 2 minutes. In an immunohistochemical (IHC) example, initial heating step raises the temperature of the thermal platforms to 75° C. for approximately 4 minutes. This initial heating step, while not necessary to remove the embedding medium, is performed in order to (1) remove any moisture which is between the biological sample and the surface of the slide; and (2) begin melting the embedding media (the melting point for paraffin is 50–57° C., as discussed previously).

The embedding media is both on the outside of the sample (i.e., encasing the sample) and also infused in the tissue. When performing this initial heating, the embedding media may pool away from the tissue. Specifically, because the slide is at a slide angle (not completely horizontal), the embedding media may slowly pool at a point on the slide which is lower than where the sample sits. In an alternate embodiment, the slide may be rinsed with a fluid (either liquid or gas) after the initial heating step to remove the embedding media that has pooled. For example, fluids such as de-ionized water may be used to rinse the embedding media from the slide.

As shown at block 64, an aqueous fluid is applied to the slide. Any aqueous fluid is acceptable such that the fluid covers the entire biological sample. As discussed previously, examples of aqueous fluid include de-ionized water, citrate buffer (pH 6.0–8.0), Tris-HCl buffer (pH 6–10), phosphate buffer (pH 6.0–8.0), SSC buffer, APK Wash™, acidic buffers or solutions (pH 1–6.9), basic buffers or solutions (pH 7.1–14), mineral oil, Norpar, canola oil, and PAG oil. Moreover, the aqueous fluid may also contain ionic or non-ionic surfactants such as Triton X-100, Tween, Brij, saponin and sodium dodecylsulfate. The surfactants lower the surface tension of the aqueous fluid, allowing the aqueous fluid to spread better over the surface of the slide. In one embodiment, the aqueous fluid includes de-ionized water with about 0.1% Triton X-100. An additional ingredient may be added, acting as an anti-microbial agent, so that the fluid prior to application on the slide does not contain microbes. In one embodiment, the fluid includes a water content, by weight, of 99% or greater (i.e., the fluid is composed of between 99%–100% water). The use of water as a fluid to remove the embedding material is unlike what is conventionally used to remove the embedding material, such as organic solvents. Water is totally immiscible with paraffin, a typical embedding material. In contrast, organic solvents, such as toluene, xylene, limonene, are miscible with paraffin and therefore considered suitable for deparaffinization.

Further, the aqueous fluid should be applied in sufficient amounts and at sufficient times (accounting for evaporation of the aqueous fluid due to heating) such that the embedding media may float to the surface of the aqueous fluid and such that the biological sample on the slide will not dry out. In one embodiment, the aqueous fluid is applied sequentially, with a first application of approximately 1 mL of aqueous fluid on the biological sample, and with a second application two minutes later of aqueous fluid. The second application may be approximately 0.5 mL to 1 mL of aqueous fluid. The fluid may be applied to the slide by using a nozzle which is position directly above the slide. In this manner, the amount of fluid dropped onto the slide may be controlled. Moreover, because the fluid embedding material (such as paraffin) may have a low surface tension, applying a stream of fluid onto the slide may not leave a sufficient amount of fluid on the top of the slide. Thus, using the nozzle to drop the fluid onto the embedded sample is preferred as it allows more of the fluid to remain on the upper surface of the slide. An additional consideration is the maintenance of the temperature of the biological sample above the melting point of the embedding media. In the paraffin example, the melting point is approximately 50–57° C. In a preferred embodiment, the sample is heated to 75° C. However, since the aqueous fluid is not heated, the application of the aqueous fluid to the slide lowers the temperature of the biological sample temporarily to approximately 60–65° C., which is still above the melting point of paraffin. Thus, the choice of temperature to heat the sample should be high enough so that the addition of fluids to the slide does not lower the temperature of the slide below the melting point of the embedding media. Alternatively, the fluid applied to the slide may be heated prior to application so as not to reduce the temperature of the sample on the slide.

At block 66, an evaporation inhibitor is applied. In a preferred embodiment, LIQUID COVERSLIP™ (LCS™) is applied. Thereafter, the system waits for a predetermined amount of time as the slide is heated, as shown at block 68. In in situ hybridization (ISH), one example of the time for heating the slide is 6 minutes at 75° C. In an immunohistochemical (IHC) example, the incubation period is 8 minutes at 75° C. In one embodiment, the temperature of the slides remains constant during the initial heating until step 76, as discussed subsequently. Thus, the heaters for the slides are turned on during the initial step of heating and remain on at the same temperature until after the embedding media is rinsed from the slide. Alternatively, the setpoint temperature of the heaters may be adjusted from the time of initial heating until after the embedding media is rinsed from the slide.

During the heating, the embedding media floats to the top of the aqueous fluid. In a preferred embodiment, the fluid which is applied to the slide has density which is greater than the embedding media. In the specific example, the fluid is mostly composed of water (e.g., 99% or greater) and the embedding media is paraffin. Paraffin, as an oil based product, is less dense than water. Thus, the paraffin rises to the top of the water after being melted.

The slide is then rinsed, as shown at block 70, carrying away the embedding media in the aqueous fluid. In a preferred embodiment, the same type of aqueous fluid used to cover the slide is also used to rinse the slide. The rinse also leaves an amount of aqueous fluid on the biological sample. In a preferred embodiment, approximately 0.25 mL is left on the slide. Thereafter, aqueous fluid is further applied to the slide, as shown at block 72. In an alternate embodiment, the rinsing of the slide may also leave a sufficient amount of aqueous fluid on the slide such that additional aqueous fluid need not be applied.

At block 74, evaporation inhibitor is applied, which in a preferred embodiment is Liquid Coverslip™ (LCS™). Thereafter, the temperature of the slide is reduced, as shown at block 76. In a preferred embodiment, this is done by reducing or eliminating the heat applied by the thermal platform 50. Moreover, in a preferred embodiment, the temperature of the slide is reduced to a predetermined temperature of 42° C. This predetermined temperature is chosen such that all slides, when processing, are at a known temperature (as opposed to being at ambient temperature, which may fluctuate). Thereafter, the apparatus waits a predetermined amount of time, as shown at block 78.

Another embodiment of the present invention relates to the exposing of biological samples without removal of the inert materials in which biological samples have been embedded for preservation and support. In a preferred embodiment of the present invention. biological samples are readied for testing by contact heating of the microscope slide on which the embedded biological samples have been placed. Other inert materials that are not removed from embedded biological samples include but are not limited to plastic or celloidin embedding media and/or other polymers and resins.

In a preferred method of the present invention, the embedded biological sample laying on the glass slide is first heated by the heating element. The heating element exposes heat on one side of the biological sample, such as by using the thermal platforms 50 disclosed in U.S. patent application Ser. No. 09/259,240, now U.S. Pat. No. 6,296,809 within an automated staining instrument (U.S. patent application Ser. No. 08/995,052, now U.S. Pat. No. 6,045,759 and No. 60/076,198) such that the sample slide is dried.

In another method of the present invention, an embedded biological sample is placed on a glass microscope slide and the microscope slide is heated on one side (e.g., by placing the slide on a thermal platform). A reagent is then placed on the biological sample slide and the biological sample slide, with the reagent, is then heated to a specified temperature (ranging from ambient to greater than 100° C.) and for a specified amount of time (ranging from 2 minutes to 12 hours). This will cause etching of the surface of the inert embedding material, and after which the etching reagent may be removed from the slide by a fluid (as a gas or liquid). As discussed previously, the amount of time and the specified temperature may be stored in memory.

In the preferred method of the present invention, reagents are used in conjunction with or without heating the embedded biological samples. Suitable reagents may include, but are not limited to, de-ionized water, citrate buffer (pH 6.0–8.0), Tris-HCl buffer (pH 6–10), phosphate buffer (pH 6.0–8.0), SSC buffer, APK Wash™, acidic buffers or solutions (pH 1–6.9), basic buffers or solutions (pH 7.1–14) mineral oil, Norpar, canola oil, and PAG oil. Each of these reagents may also contain ionic or non-ionic surfactants such as Triton X-100, Tween, Brij, saponin and sodium dodecylsulfate.

In the method of the present invention, the temperature of the heating element is set to an appropriate level for the drying or the etching of the embedded biological sample. For example, etching may be carried out with a basic solution of methanol sodium hydroxide (sodium methoxide) at temperatures ranging from ambient to 37° C.

In the method of the present invention, the duration of time required to etch the inert material will vary according to the temperature used and the embedding material (plastic or celloidin embedding media and/or other polymers and resins, etc.). In a preferred method of the present invention the embedded biological sample is subjected to appropriate temperatures ranging from 2 minutes to 12 hours. The heating element used in the method of the present invention requires that sufficient contact be maintained between the surface on which the biological sample is placed and the heating element.

In still an alternative embodiment, the invention does not utilize direct heating of the biological sample to effect deparaffinization. The alternative embodiment is directed to an automated method of removing embedding media from a biological sample on a microscope slide, the method comprising the steps of heating an immiscible fluid to a temperature above the melting point of the embedding media; and contacting the biological sample with the heated immiscible fluid thereby liberating the embedding media from the biological sample. If the embedding media is paraffin, which has a melting point of between 50–57° C., the fluid should be greater than the melting point of paraffin (e.g., between 60–70° C.). The heating of the fluid may be performed in a variety of manners. One example is disclosed in U.S. Pat. No. 5,595,707, which is incorporated by reference in its entirety. As shown in U.S. Pat. No. 5,595,707, FIGS. 19A and 19B show different embodiments for heating liquid prior to rinsing of a sample.

As discussed previously, examples of aqueous fluid include de-ionized water, citrate buffer (pH 6.0–8.0), Tris-HCl buffer (pH 6–10), phosphate buffer (pH 6.0–8.0), SSC buffer, APK Wash™, acidic buffers or solutions (pH 1–6.9), basic buffers or solutions (pH 7.1–14), mineral oil, Norpar, canola oil, and PAG oil. Moreover, the aqueous fluid may also contain ionic or non-ionic surfactants such as Triton X-100, Tween, Brij, saponin and sodium dodecylsulfate. The surfactants lower the surface tension of the aqueous fluid, allowing the aqueous fluid to spread better over the surface of the slide. In one embodiment, the aqueous fluid includes de-ionized water with about 0.1% Triton X-100. An additional ingredient may be added, acting as an anti-microbial agent, so that the fluid prior to application on the slide does not contain microbes. In one embodiment, the fluid includes a water content, by weight, of 99% or greater (i.e., the fluid is composed of between 99%–100% water).

Contacting may, in one embodiment, include rinsing of the biological sample with fluid. Rinsing may comprise a continuous stream of fluid or a series of streams of fluid. The rinsing may be performed by using a nozzle or series of nozzles which direct the fluid onto the slide. In a preferred embodiment, the fluid is directed onto the biological sample at an angle (e.g., between 15 and 25 degrees). Alternatively, the nozzle may be placed directly above the sample and the fluid may be dropped onto the sample. The term "liberating" means creating the appropriate conditions for allowing the embedding media to free itself from the tissue. This occurs when the heated immiscible liquid, usually a buffer, is rinsed over the surface of the sample, thereby simultaneously melting the embedding media and providing the removal means for floating the now liquid embedding media away from the tissue.

The instrument may be modified to add a liquid recirculating pump that will heat and recirculate the buffer to maintain the temperature of the EZ Prep buffer above the melting point of the embedding medium (for paraffin at least about 65 degrees C.). The EZ Prep is then contacted with the biological sample preferably by rinsing the sample on the slide for a sufficient time period to heat the sample above the melting point of the paraffin, and simultaneously rinse away the melting paraffin from the sample. Example 10 teaches one way this alternative embodiment was actually performed.

In one embodiment, the invention utilizes both direct heating of the biological sample and heating of the fluid to effect deparaffinization. The direct heating of the biological sample and heating of the fluid work in combination to melt away the embedding media. The heating of the biological sample may be either above or below the melting point of the embedding medium. Likewise the heating of the fluid may be either above or below the melting point of the embedding medium. For example, there may be four different possibilities when deparaffinization is achieved by both heating of the biological sample and heating of the fluid: (1) heating of the biological sample to less than the melting point of the embedding medium and heating of the fluid to less than the melting point of the embedding medium; (2) heating of the biological sample to less than the melting point of the embedding medium and heating of the fluid to greater than the melting point of the embedding medium; (3) heating of the biological sample to greater than the melting point of the embedding medium and heating of the fluid to less than the melting point of the embedding medium; and (4) heating of the biological sample to greater than the melting point of the embedding medium and heating of the fluid to greater than the melting point of the embedding medium.

A preferred embodiment of the present invention also comprises an automated method of cell conditioning, either concurrent with, subsequent to or independent of removal or etching of the inert embedding material from the biological sample. Heating the biological sample in an appropriate (organic or inorganic) reagent has been found to improve the accessibility of the reagent to the target molecule in the cell (protein, nucleic acid, carbohydrate, lipid, pigment or other small molecule, etc.). This process of improving accessibility of the reagent (organic or inorganic) to the molecular target is referred to herein as cell conditioning.

In one method of the present invention, cell conditioning is accomplished while the biological sample is being exposed as described above. In this method of the present invention, a biological sample is placed on a glass microscope slide and the microscope slide is heated on one side (e.g., by placing the slide on a thermal platform) within an automated staining instrument (U.S. patent application Ser. No. 08/995,052, now U.S. Pat. No. 6,045,759 and No. 60/076,198). A reagent is placed on the biological sample and the temperature of the heating element may or may not be increased. The biological sample is exposed to the appropriate temperature for an appropriate duration of time that will permit the melting or etching of the inert material and permit cell conditioning of the biological sample to be subsequently stained using histological or cytological techniques.

Figure 7A:
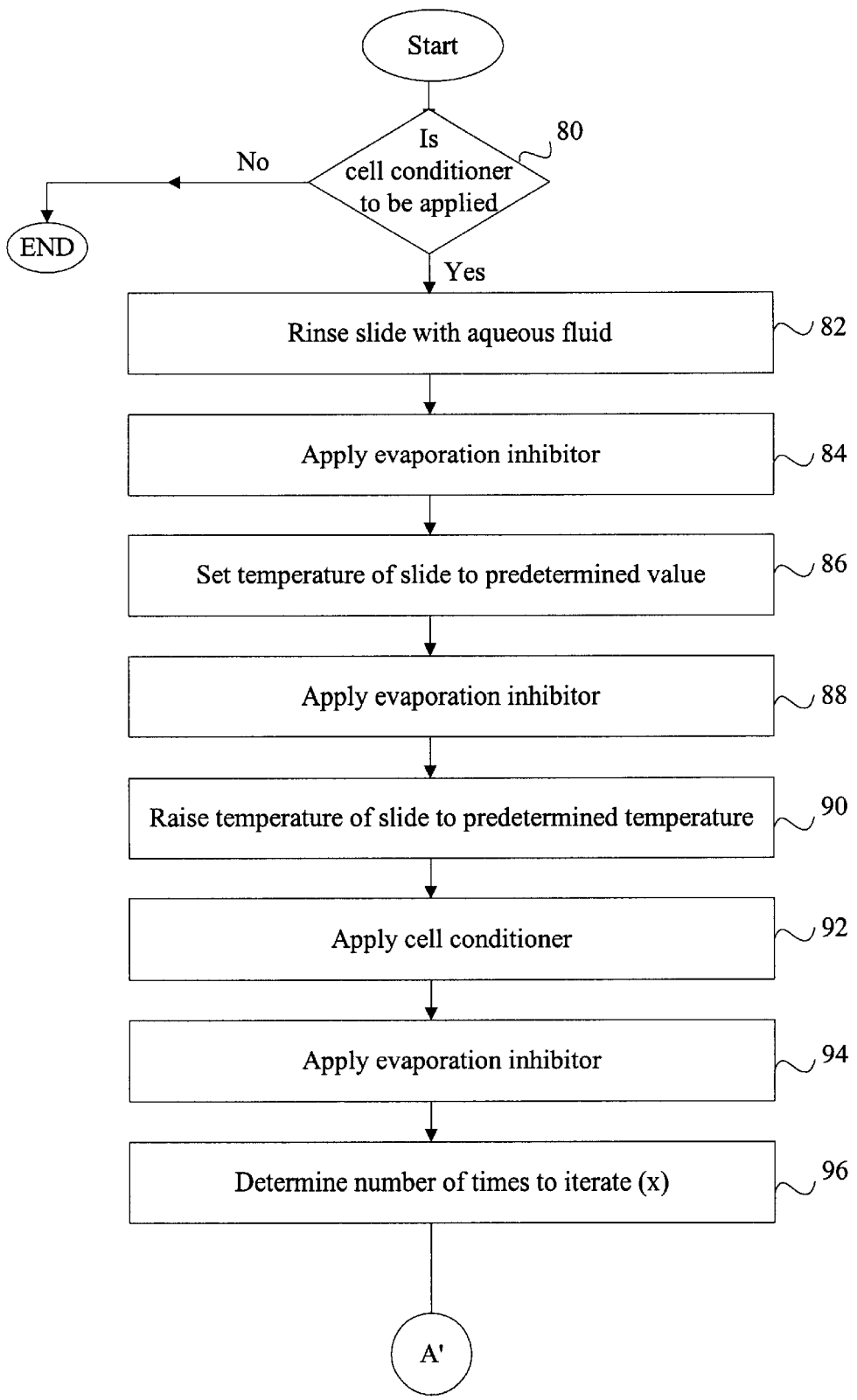
FIGS. 7a–b are flow charts for one embodiment for cell conditioning.
Figure 7B:
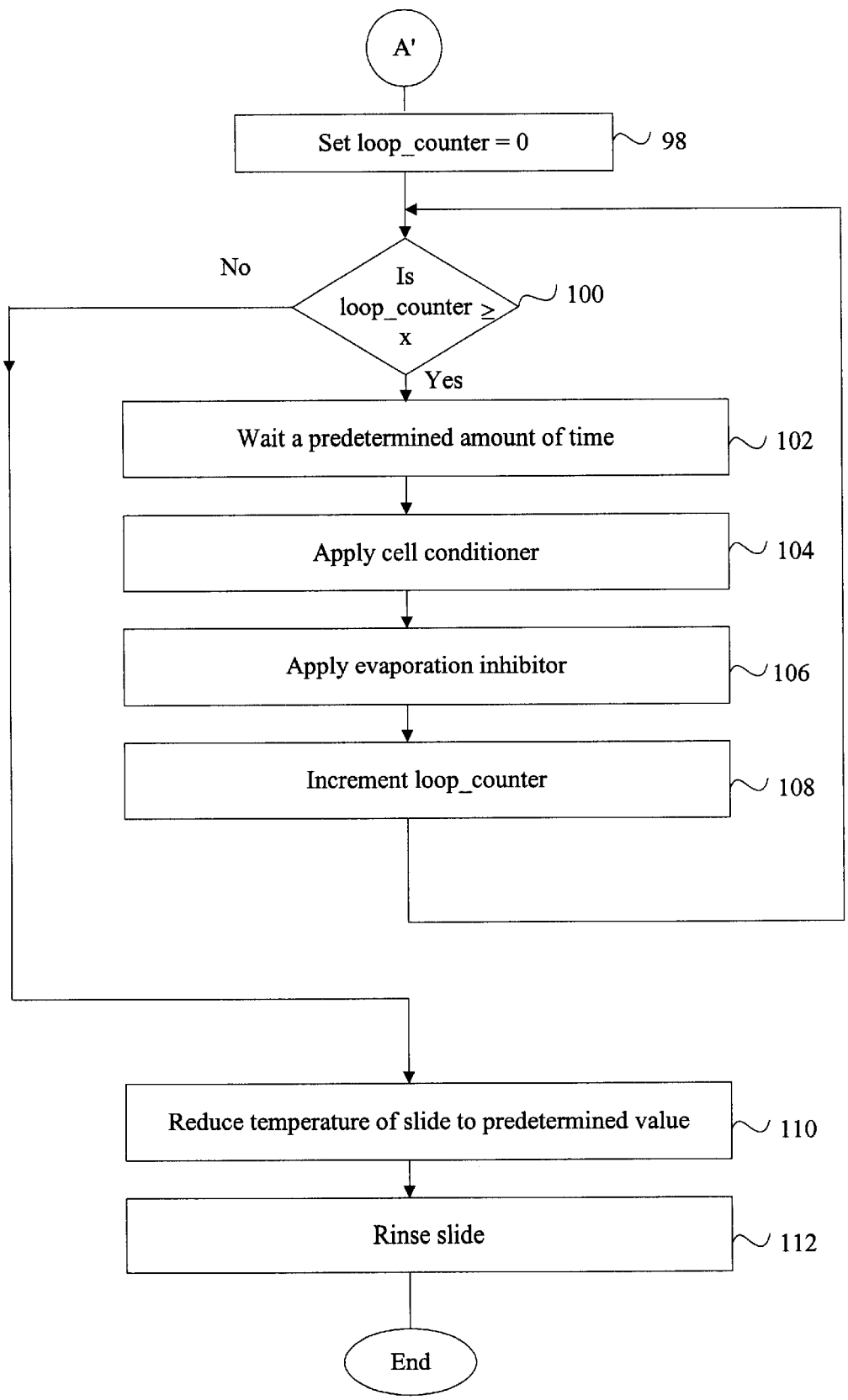

Referring to FIGS. 7a–b, there are shown flow charts of one embodiment for exposing a biological sample to permit cell conditioning. As shown at block 80, it is determined whether cell conditioning is applied. A variety of cell conditioners may be applied depending on the processing necessary. As shown at block 82, the slide is rinsed with aqueous fluid. Any aqueous fluid is acceptable such that the fluid covers the entire biological sample. In a preferred embodiment, de-ionized water with Triton X-100™ is used. Thereafter, an evaporation inhibitor is applied to the slide, as shown at block 84. In a preferred embodiment, Liquid Coverslip™ is applied. Thereafter, the temperature of the slide is modified to a predetermined value, as shown at block 86. In a preferred embodiment, heaters heat the slide to 42° C. This initial heating is performed in order to ensure that all of the slides begin the cell conditioning at a predetermined temperature; otherwise, the temperature of the slide may be unknown if the temperature of the slides is determined by the ambient temperature.

Evaporation inhibitor is then applied, as shown at block 88. Thereafter, the temperature of the slides is raised to a predetermined temperature, as shown at block 90. This is the temperature at which the cell conditioning is performed. In a preferred embodiment, the temperature of the heaters is set to 100° C. Thereafter, cell conditioner is applied, as shown at block 92 and evaporation inhibitor is applied, as shown at block 94. A multitude of cell conditioners may be applied, as discussed herein.

How lightly/heavily a sample is fixed determines the amount of cell conditioning necessary. If a sample is lightly fixed, a mild cell conditioning is recommended. Likewise, if the sample is moderately or heavily (extended) fixed, a moderate or a heavy cell conditioning, respectively, is recommended. Improper cell conditioning may have adverse consequences on the processing of the sample. In a preferred embodiment, cell conditioning mild/medium/heavy time is 30/60/90 minutes respectively. Moreover, the cell conditioner is applied at predetermined increments within the processing in order to properly condition the cell and to avoid drying out the sample. As shown in FIG. 7a, the number of times to iterate through the application of cell conditioner and LCS™ is determined, as shown at block 96. This variable is called "loop_counter." Loop_counter is set to 0, as shown at block 98 in FIG. 7b. A loop is entered (as shown at block 100) and the system waits a predetermined amount of time (as shown at block 102). In a preferred embodiment, the predetermined amount of time is 6 minutes. Cell conditioner is applied (as shown at block 104) and evaporation inhibitor is applied (as shown at block 106). The loop_counter is then incremented, as shown at block 108. In a preferred embodiment, the number of times the loop is executed is 5/10/15 for mild/medium/heavy cell conditioning. Thereafter, the temperature of the slide is reduced, as shown at block 110. In a preferred embodiment, the heater temperature is reduced to 42° C. Alternatively, the heater may be turned off and the slide temperature may revert to the ambient temperature. Thereafter, the slide is rinsed, as shown at block 112.

The reagents used for cell conditioning can be the same as those for exposing the embedded biological sample. For example, for DNA targets, a cell conditioning solution may be a solution of EDTA; a common temperature setting may be 95° C. for a duration ranging from 2–90 minutes. For protein targets, a cell conditioning solution may be a solution of boric acid buffer; a common temperature setting may be in excess of 100° C. for a duration ranging from 2–90 minutes. For RNA targets, a cell conditioning solution may be a solution of SSC; a common temperature setting may be 75° C. for a duration ranging from 2–90 minutes. For histochemical reactions, such as a Hematoxylin and Eosin (H&E) stain, a cell conditioning solution may be treated de-ionized water; a common temperature may range from 60–80° C. for a duration of 2–90 minutes. A partial list of possible reagents appears in Analytical Morphology, Gu, ed., Eaton Publishing Co. (1997) at pp. 1–40. The solutions should generally be of known molarity, pH, and composition. Sodium dodecyl sulfate (SDS) and/or ethylene glycol is preferably added to the conditioning solution. In addition, metal ions or other materials may be added to these reagents to increase effectiveness of the cell conditioning.

In another method of the present invention, cell conditioning is accomplished subsequent to the biological sample being exposed as described above. In this method of the present invention a biological sample is placed on a glass microscope slide and the microscope slide is heated on one side (e.g., by placing the slide on a thermal platform) within an automated staining instrument (U.S. patent application Ser. No. 08/995,052, now U.S. Pat. No. 6,045,759 and No. 60/076,198). In this method (one embodiment of which is shown in FIG. 6), the embedded biological sample laying on the glass slide is first heated by the heating element within an automated staining instrument such that the sample slide is dried and the embedding material is melted or etched and removed by the application of a fluid. Subsequent to exposing the biological sample, an appropriate reagent is applied in order to permit cell conditioning of the biological sample to be subsequently stained using histological or cytological techniques.

The reagents used for cell conditioning can be the same as those for exposing the embedded biological sample. For example, for DNA targets, a cell conditioning solution may be a solution of SSC; a common temperature setting may be 95° C. for a duration ranging from 2–90 minutes. For protein targets, a cell conditioning solution may be a solution of phosphate buffer; a common temperature setting may be in excess of 100° C. for a duration ranging from 2–90 minutes. For RNA targets, a cell conditioning solution may be a solution of SSC; a common temperature setting may be 75° C. for a duration ranging from 2–90 minutes. For histochemical reactions, such as a Trichrome stain, a cell conditioning solution may be Bouins; a common temperature may range from 60–80° C. for a duration of 2–30 minutes.

In yet another method of the present invention, cell conditioning is accomplished without the biological sample being exposed. In this method of the present invention, a biological sample is placed on a glass microscope slide and the microscope slide placed on a heating element within an automated staining instrument. A reagent is placed on the biological sample and the temperature of the heating element may or may not be increased. Cell conditioning of the biological sample may be performed prior to being stained using histological or cytological techniques.

The reagents used for cell conditioning can be the same as those for exposing the embedded biological sample. For example, for DNA targets, a cell conditioning solution may be a solution of sodium citrate; a common temperature setting may be 90° C. for a duration ranging from 2–90 minutes. For protein targets, a cell conditioning solution may be a solution of urea; a common temperature setting may be in excess of 100° C. for a duration ranging from 2–90 minutes. For whole cells, a cell conditioning solution may be a solution of methanol; a common temperature setting may be ambient for a duration ranging from 4–10 minutes. For histochemical reactions, such as an Acid Fast Bacilli (AFB) stain, a cell conditioning solution may be peanut oil; a common temperature may range from 60–70° C. for a duration of 30–60 minutes.

The present invention also comprises cell conditioning of cytological preps, such as fine needle aspirations (FNA) smears, touch preps, Ficoll, Cytospins®, Thins Preps®, cervical-vaginal pap smears, blood or body fluid films, etc., that are neither fixed with an aldehyde nor embedded in a matrix, such as paraffin. Many are fixed in an alcohol, such as methanol or ethanol, others will be sprayed with hair spray or other aerosol fixative and dried, and still others will be placed in cytological fixatives, which may include carbowax and Saccomanno's (organic or inorganic) reagent among others. The cells are either centrifuged or filtered to a slide or directly touched to a glass slide and smeared in some cases (PAP's) or applied directly against the slide (touch preps).

The term "Biological sample" includes, but is not limited to, any collection of cells (either loose or in tissue) that can be mounted on a standard glass microscope slide including, without limitation, sections of organs, tumors sections, bodily fluids, smears, frozen sections, blood, cytology preps, microorganisms, tissue arrays and cell lines.

The term "Stain" includes, but is not limited to, any biological or chemical entity which, when applied to targeted molecules in biological sample, renders the molecules detectable under microscopic examination. Stains include without limitation detectable nucleic acid probes, antibodies, and other reagents which in combination or by themselves result in a colored end product (by bright field or fluorescence).

The terms "Reagent", "Buffer", "Additive", "Component" and "Solution" as used herein for exposing or deparaffinizing (i.e., the process of deparaffinization) may comprise the following component or components, all of which are available from Sigma Chemical, unless otherwise noted: de-ionized water, de-ionized water with about 0.1% Triton X-100, 10 mM phosphate at around pH 6.1, 10 mM phosphate with about 0.1% Triton X-100 at around pH 6.1, 10 mM citrate at around pH 6, 10 mM citrate with about 0.1% Triton X-100, 2×SSC. 10 mM Tris[hydroxymethyl] aminomethane chloride (i.e., Tris-Cl) at around pH 8.2, 10 mM Tris-Cl with about 0.1% Triton X-100 at around pH 8.2. A person skilled in the art to which this invention pertains will recognize that the concentration or concentrations of the component or components listed above may be varied without altering the characteristics of the reagent, buffer, additive or solution for exposing or deparaffinizing.

The terms "Reagent", "Buffer", "Additive", "Component", "Solution" and "Cell Conditioner" as used herein for cell conditioning may comprise the following component or components, all of which are available from Sigma Chemical, unless otherwise noted: 5 mM citrate at around pH 6, 5 mM citrate with about 0.5% sodium dodecyl sulfate (SDS) at around pH 6, 10 mM citrate at around pH 6, 10 mM citrate with about 0.5% SDS at around pH 6, 20 mM citrate at around pH 6, 20 mM citrate with about 0.5% SDS at around pH 6, 50 mM citrate at around pH 6, 50 mM citrate with about 0.5% SDS at around pH 6, 1 mM ethylene diamine tetraacetic acid (EDTA) at around pH 8, 1 mM EDTA with about 0.075% SDS at around pH 8, 10 mM EDTA at around pH 8, 10 mM EDTA with about 0.075% SDS at around pH 8, 20 mM EDTA at around pH 8, 20 mM EDTA with about 0.075% SDS at around pH 8, 50 mM EDTA at around pH 8, 50 mM EDTA with about 0.075% SDS at around pH 8, 10 mM citrate with about 0.5% SDS and about 1% ethylene glycol at around pH 6, 10 mM citrate with about 0.5% SDS and about 5% ethylene glycol at around pH 6, 10 mM citrate with about 0.5% SDS and about 10% ethylene glycol at around pH 6, 1 mM EDTA with about 0.075% SDS and about 1% ethylene glycol at around pH 8, 1 mM EDTA with about 0.075% SDS and about 5% ethylene glycol at around pH 8, 1 mM EDTA with about 0.075% SDS and about 10% ethylene glycol at around pH 8, phosphate/citrate/EDTA at about pH 9, 10 mM citrate with about 10 mM urea at around pH 6, 10 mM citrate with about 1 mM urea at around pH 6.2, 10 mM sodium citrate with about 1.4 mM $MgCl_2$ and about 0.1% SDS at around pH 7, 10 mM sodium citrate with about 1.4 mM $MgCl_2$ and about 0.1 % SDS at around pH 7.99, 10 mM Tris-Cl at around pH 8, 10 mM Tris-Cl with about 20% formamide at around pH 8, 10 mM citrate with about 5% dimethyl sulfoxide (DMSO) at around pH 6, 10 mM citrate with about 0.1% Triton X-100 and about 20% formamide at around pH 6, 10 mM phosphate with 5×SSC and about 2.5% chrondroitin A at around pH 7, 10 mM Tris-Cl with about 10 mM EDTA and about 0.1 % Triton X-100 and about 20% formamide at around pH 8.2, 10 mM citrate with about 20% glycerol at around pH 6, 10 mM citrate with about 0.1% Triton X-100 and about 10 mM glycine at around pH 6, 1 mM EDTA with about 1 mM citrate and about 0.25% SDS at around pH 7.8, Norpar/mineral oil (high temperature coverslip), PAG-100 oil, 10 mM citrate with about 2% SDS at a pH of around 6 to around 6.2, 10 mM citrate with about 1% SDS at a pH of around 6 to around 6.2, 10 mM citrate with about 0.5% SDS at a pH of around 6 to around 6.2, 10 mM citrate with about 0.25% SDS at a pH of around 6 to around 6.2, 1 mM EDTA with about 2% SDS at a pH of around 7.5 to around 8, 1 mM EDTA with about 1% SDS at a pH of around 7.5 to around 8, 1 mM EDTA with about 0.5% SDS at a pH of around 7.5 to around 8, 1 mM EDTA with about 0.25% SDS at a pH of around 7.5 to around 8, 1 mM EDTA with about 0.1% SDS at a pH of around 7.5 to around 8, 1 mM EDTA with about 0.075% SDS at a pH of around 7.5 to around 8, 0.5 mM EDTA with about 0.25% SDS at around pH 8, 10 mM EDTA with about 0.5% SDS at around pH 9.6. A person skilled in the art to which this invention pertains will recognize that the concentration or concentrations of the component or components listed above may be varied without altering the characteristics of the reagent, buffer, additive or solution for cell conditioning.

A preferred embodiment of the present invention is the basic formulation comprising 10 mM Tris base, 7.5 mM boric acid, 1 mM EDTA (disodium salt), 0.05% ProClin™ 300 (Supelco, Inc., Bellefonte, Pa.) at pH 8.5. Other embodiments contemplated include the basic formulation wherein the Tris base concentration ranges from about 5 mM to about 20 mM, wherein the boric acid concentration ranges from about 5 mM to about 40 mM, wherein the EDTA concentration ranges from about 0.5 mM to about 2 mM or wherein the pH ranges from around pH 7 to around pH 9. Temperature ranges contemplated are from around 95° C. to around 100° C. Without intending to be construed as a limitation, it should be noted that no significant difference is seen when the concentration of Tris base or EDTA varies over the range specified above, significantly better results were obtained when the concentration of boric acid was 10 mM as opposed to 20 mM or 40 mM, slightly better results were obtained when the concentration of boric acid was 10 mM as opposed to 5 mM, conditioning is optimal at a pH of around 8 to around 8.6. Comparing 10 mM Tris+20 mM boric acid+1 mM EDTA+0.5% Brij 35 with 10 mM Tris+20 mM boric acid+0.5% Brij 35, both reagents displayed strongest conditioning at 100° C. with significantly weaker conditioning at 95° C.

Other embodiments contemplated include, but are not limited to, citrate buffer (a combination of sodium citrate trisodium salt dihydrate and citric acid monohydrate hydrate), 10 mM Tris+20 mM boric acid+1 mM EDTA, 10 mM Tris+20 mM boric acid, 10 mM Tris+1 mM EDTA, 10 mM Tris, 20 mM boric acid, 1 mM EDTA, 20 mM Tris+20 mM boric acid+1 mM EDTA, 5 mM Tris+20 mM boric acid+1 mM EDTA, 10 mM Tris+20 mM boric acid+2 mM EDTA, 10 mM Tris+20 mM boric acid+0.5 mM EDTA, 10 mM Tris+40 mM boric acid+1 mM EDTA, 10 mM Tris+10 mM boric acid+1 mM EDTA, 10 mM Tris+5 mM boric acid+1 mM EDTA, 10 mM Tris+7.5 mM boric acid+1 mM EDTA, 10 mM Tris+20 mM boric acid+1 mM EDTA+5% ethylene glycol, 10 mM Tris+20 mM boric acid+5% ethylene glycol, 10 mM Tris+20 mM boric acid+1 mM EDTA+0.1% SDS, 10 mM Tris+20 mM boric acid+0.1% SDS, 10 mM Tris+20 mM boric acid+1 mM EDTA+5% DMSO, 10 mM Tris+20 mM boric acid+5% DMSO, 10 mM Tris+20 mM boric acid+1 mM EDTA+10% DMSO, 10 mM Tris+20 mM boric acid+10% DMSO, 10 mM Tris+20 mM boric acid+1 mM EDTA+5% formamide, 10 mM Tris+20 mM boric acid+5% formamide, 10 mM Tris+20 mM boric acid+1 mM EDTA+10% formamide, 10 mM Tris+20 mM boric acid+10% formamide, 10 mM Tris+20 mM boric acid+1 mM EDTA+0.5% Brij 35, 10 mM Tris+20 mM boric acid+0.5% Brij 35, 10 mM Tris+20 mM boric acid+1 mM EDTA+0.1% Brij 35, 10 mM Tris+20 mM boric acid+0.1% Brij 35, 10 mM Tris+20 mM boric acid+1 mM EDTA+0.5% Triton X-100, 10 mM Tris+20 mM boric acid+0.5% Triton X-100.

The term "10×SSC" refers to a 10 molar concentration of sodium chrloide/sodium citrate solution, comprising deionized water as needed to make a liter solution, 87.66 g NaCl, 44.12 g citric acid trisodium salt, dihydrate, adjusted to pH 7.0 with HCl or NaOH, as appropriate. 0.5 ml ProClin 300 is added as preservative. For all phosphate buffers prepared at any concentration (X molar), prepare X molar solutions of (1) $HPO_4^{-2}$ using $K_2HPO_4$ or $NaHPO_4$, and (2) $H_2PO_4^-$ using $KH_2PO_4$ or $NaH_2PO_4$.

Another preferred embodiment of the cell conditioner (cell conditioning solution 2 or CC2) comprises about 10 mM citrate buffer at about pH 6, about 5% ethylene glycol, about 1 mM sodium metabisulfite (Morphosave™, Ventana Medical Systems, Inc., Tucson, Ariz.; U.S. Pat. No. 5,432,056) and about 0.3% sodium dodecyl sulfate (SDS). The concentration of citrate may range from about 5 mM to about 50 mM. The pH of the buffer may range from about 4 to about 8. The concentration of ethylene glycol may range from about 1% to about 10%. The concentration of sodium metabisulfite may range from about 0.1 mM to about 10 mM, preferably from about 0.5 mM to about 1.5 mM. The concentration of SDS may range from about 0.1% to about 1%, preferably from about 0.25% to about 0.5%.

The following examples are presented for illustrative purposes only and are not intended, nor should they be construed, as limiting the invention in any way. Those skilled in the art will recognize that variations on the following can be made without exceeding the spirit or scope of the invention. All patents, patent applications, and other publications are hereby incorporated by reference in their entirety.

EXAMPLES

Example 1

Automated "Exposing" and "Cell Conditioning" with Biological Samples Stained with H&E Biological samples, including breast, stomach, brain, tonsil and kidney, that had been embedded in paraffin were exposed according to the following procedure: slides containing the above referenced biological sample were placed on an automated instrument (Ventana Medical Systems, Inc., Tucson, Ariz.) and subjected to the exposing protocol described below. Generally, the slides containing paraffin embedded biological samples were dry heated to 65° C. for six (6) minutes then rinsed with any of the following: 1) 1× citrate buffer, 2) de-ionized water, 3) 10 mM phosphate buffer (pH=6.3), or 4) 10 mM Tris-HCl buffer (pH=7.4) each containing 0.1% Triton X-100.

EXPOSING PROTOCOL 1

1. Incubate for 2 minutes
2. Rinse slide
3. Adjust slide volume and apply LIQUID COVERSLIP™
4. Incubate for 6 minutes
5. Rinse slide
6. Adjust slide volume and apply LCS™
7. Increase temperature to 65.0° C.
8. Rinse slide
9. Adjust slide volume and apply LCS™
10. Incubate for 4 minutes
11. Adjust slide volume and apply LCS™
12. Incubate for 4 minutes
13. Adjust slide volume and apply LCS™
14. Incubate for 4 minutes
15. Rinse slide
16. Decrease temperature to 42.0° C.
17. Adjust slide volume and apply LCS™
18. Incubate for 4 minutes
19. Rinse slide
20. Decrease temperature to 42.0° C.
21. Adjust slide volume and apply LCS™
22. Incubate for 4 minutes
23. Rinse slide After automated exposing, the biological sample was stained with hematoxylin and eosin by the following method. Slides were placed in hematoxylin 1 (Richard Allen Scientific, Kalamazoo, Mich.) for 1.5 minutes and then rinsed with running de-ionized water for one minute. Slides were then placed in acid alcohol clarifier (Richard Allen Scientific) for one minute and then rinsed with running de-ionized water for one minute. Slides were then placed in diluting ammonia-bluing reagent for one minute (Richard Allen Scientific, Kalamazoo, Mich.) and then rinsed in running de-ionized water for one minute. Slides were then rinsed in 95% ethanol, and then placed in 2.5% eosin Y (Richard Allen Scientific, Kalamazoo, Mich.) for 2.5 minutes. The biological samples on the slides were dehydrated by exposing the biological sample to a 100% ethanol bath for one minute. This process was repeated three times followed by exposure of the biological sample to a xylene bath for three minutes, twice. After the dehydration step the biological sample was covered with a coverslip.

Control biological samples were deparaffinized by a traditional solvent-based deparaffinization technique. Paraffin-embedded biological samples placed on microscope slides and preserved in paraffin were completely submersed in a xylene bath for five minutes. Slides containing biological samples were placed in a second xylene bath for five minutes. After removal from the second xylene bath, the slides were placed in a 100% ethanol bath for three minutes. Slides were then placed in a second 100% ethanol bath for three minutes and then placed in a 90% ethanol solution for two minutes. The slides were then placed in 80% ethanol for one minute followed by complete immersion in distilled water for one to three minutes. After deparaffinization, the biological samples were stained with hematoxylin and eosin as described above.

The biological samples that were deparaffinized by the solvent technique and by the automated heating technique were compared after staining by hematoxylin and eosin. Morphology on all sets of slide was acceptable and essentially equivalent. The tonsil and brain biological samples that were exposed by the automated heating method showed more intensified hematoxylin staining than the biological samples deparaffinized by standard solvent techniques.

Example 2

Automated "Exposing" of Biological Samples with Simultaneous "Cell Conditioning"

Biological samples of kidney and tonsil that had been formalin fixed and embedded in paraffin were exposed according to the protocol described in Example 1. After automated exposing, the biological sample was subjected to the automated DAB paraffin protocol used for immunohistochemical staining. The protocol for DAB staining is described below:

DAB Protocol

1. Incubate for 2 minutes
2. Rinse slide
3. Adjust slide volume and apply LCS™
4. Rinse slide
5. Adjust slide volume and apply LCS™
6. Rinse slide
7. Adjust slide volume and apply LCS™
8. Apply one drop of inhibitor
9. Incubate for 4 minutes
10. Adjust slide volume and apply LCS™
11. Apply one drop of primary antibody
12. Incubate for 32 minutes
13. Adjust slide volume and apply LCS™
14. Apply one drop of Biotinylated Ig
15. Incubate for 8 minutes
16. Rinse slide
17. Adjust slide volume and apply LCS™
18. Apply one drop of Avidin-HRPO
19. Incubate for 8 minutes
20. Rinse slide
21. Adjust slide volume and apply LCS™
22. Apply one drop of DAB and one drop DAB $H_2O_2$
23. Incubate for 8 minutes
24. Rinse slide
25. Adjust slide volume and apply LIQUID COVERSLIP™
26. Apply one drop of Copper
27. Incubate for 4 minutes
28. Rinse slide The primary antibody used for the kidney biological sample was Anti-CD15 (Ventana Medical Systems, Inc. Tucson, Ariz., Catalogue no. 250-2504). The primary antibody used for the tonsil biological sample was Anti-CD45RO (Ventana Medical Systems, Inc. Tucson, Ariz., Catalogue no. 250-2563). The DAB staining kit used was obtained from Ventana Medical Systems, Inc. Tucson, Ariz., Catalogue no. 250-001.

Control biological samples were deparaffinized by a traditional solvent-based deparaffinization technique, as described in Example 1. After deparaffinization the biological samples were placed in a pressure cooker (Model #62104 Nordic Ware, Minneapolis, Minn.) containing 1.5 L 1× citrate buffer. The pressure cooker was then sealed and placed in a microwave oven (Model #MQSO836E, Matsushita, Franklin Park, Ill.). With the microwave oven set on "high," the samples were subjected to microwave heating for approximately 30 minutes. After microwaving the samples were then "cured" for 30 minutes in the pressure cooker with the lid securely fastened. After curing the biological samples were placed in 1× citrate buffer for two minutes. The biological samples were then removed from the citrate buffer and the end of the slides blotted to removed excess citrate buffer. After blotting, the slides were placed on the automated instrument and immunohistochemically stained as described above.

The biological samples deparaffinized by the solvent technique and by the automated exposing and simultaneous cell conditioning technique were compared after immunohistochemical staining. Morphology and staining on all sets of slides was acceptable and essentially equivalent.

Example 3

Two Step Automated "Exposing" and "Cell Conditioning"

Biological samples of tonsil and breast that had been preserved in paraffin and treated with formaldehyde were treated by the following protocol:

Exposing and Cell Conditioning Protocol 5 1. Incubate for 2 minutes
2. Increase thermofoil temperature to 65.0° C.
3. Incubate for 6 minutes
4. Rinse slide and apply LCS™
5. Incubate for 6 minutes
6. Rinse slide and apply LCS™
7. Increase thermofoil temperature to 100.0° C.
8. Adjust slide volume and apply LCS™
9. Rinse slide
10. Adjust slide volume and apply LCS™
11. Incubate for 4 minutes
12. Adjust slide volume and apply LCS™
13. Incubate for 4 minutes
14. Adjust slide volume and apply LCS™

15. Incubate for 4 minutes
16. Adjust slide volume and apply LCS™
17. Incubate for 4 minutes
18. Adjust slide volume and apply LCS™
19. Incubate for 4 minutes
20. Adjust slide volume and apply LCS™
21. Incubate for 4 minutes
22. Adjust slide volume and apply LCS™
23. Incubate for 4 minutes
24. Adjust slide volume and apply LCS™
25. Incubate for 4 minutes
26. Adjust slide volume and apply LCS™
27. Incubate for 4 minutes
28. Rinse slide
29. Decrease temperature to 42.0° C.
30. Adjust slide volume and apply LCS™
31. Incubate for 4 minutes
32. Rinse slide
33. Decrease temperature to 20.0° C.
34. Adjust slide volume and apply LCS™
35. Incubate for 4 minutes
36. Rinse slide The buffer used in the protocol was SSC buffer with either 20% formamide or 0.1% Triton. After the biological sample was subjected to the above protocol, the DAB paraffin protocol used for immunohistochemical staining of Example 2 was applied. Tonsil biological sample was treated with anti-Ki67 as a primary antibody. Breast samples were treated with anti-estrogen receptor (6F11) or anti-progesterone receptor (1A6) as a primary antibody. All primary antibodies are available through Ventana.

Control biological samples were deparaffinized by a traditional solvent-based de-paraffinization technique, as described in Example 1. After deparaffinization the biological samples were placed in a pressure cooker (Model #62104 Nordic Ware, Minneapolis, Min.) containing 1.5 L 1x citrate buffer. The pressure cooker was then sealed and placed in a microwave oven (Model #MQSO836E, Matsushita, Franklin Park, Ill.). With the microwave oven set on "high", the samples were subjected to microwave heating for approximately 30 minutes. After microwaving the samples were then "cured" for 30 minutes in the pressure cooker with the lid securely fastened. After curing the biological samples were placed in 1x citrate buffer for two minutes. The biological samples were then removed from the citrate buffer and the end of the slides were blotted to removed excess citrate buffer. After blotting the slide were placed on the automated instrument and immunohistochemically stained as described above.

The biological samples deparaffinized by solvent technique and by the automated heating technique were compared after immunohistochemical staining. Morphology on all sets of slide was acceptable and essentially equivalent. Staining with Ki67 on all sets of slides was equivalent. ER (6F11) and PR (1A6) staining was slightly weaker with automated cell conditioning indicating the process does work but more development and optimization is required.

Example 4

Automated Cell Conditioning of Non Paraffin Embedded Cell Lines for in situ Hybridization (Thin Preps™)

Hela (ATCC lot # 980427H), Caski (ATCC lot # 980416C) and Siha (ATCC lot # 980416S) cell lines stored in Cytyk preparation solution (lot # 01139Q) were deposited on microscope slides using the Cytyk 2000 instrument. After deposition the slides were placed in alcohol to keep moist until use on the Discovery® In-Situ staining module (Ventana Medical Systems Inc., Tucson, Ariz.). Slides were loaded into the instrument and wetted with 2xSSC made from 20xSSC (Ventana P/N 650-012). Slides were run through a cell conditioning protocol currently referred to as Depar 30 where the slides are rinsed with 2xSSC and the temperature of the slides is increased to 95° C. for a period of approximately 30 minutes. The slides are then cooled to 37° C. and rinsed with APK Wash® prior to the in-situ staining run.

Using the protocol Blue Swap ISH the cell lines were stained for HPV 16/18 (Enzo HPV 16/18 Bio Probe cat # 32874). Prior to probe application the cell lines are enzymatically digested with Protease 2 (Ventana P/N 250-2019). After the probe application the probe and biological sample are denatured simultaneously at 95° C. for 8 minutes. The non-specifically bound probe is washed off with stringency washes of 2xSSC at 55° C. The probe is then detected with Streptavidin Alk Phos and NBT/BCIP.

The cell lines were dehydrated after staining with a one-minute exposure to 95% ethanol and a one-minute exposure to 100% ethanol repeated 2 times. Following the ethanol the slides were exposed to xylene for 3 minutes twice. After dehydration the slides were coverslipped.

The stained cell lines after conditioning showed acceptable morphology, weak staining and there was high background on these slides indicating a need for the process to be developed more.

Depar 30 Protocol
Wet Load Slides
1. Skip Application & Incubate for 2 minutes
2. Rinse Slides (2xSSC Buffer) (Warm Slides to 65° C.)
3. Adjust Slide Volume, then apply LCS™
4. Skip Application & Incubate 6 minutes
5. Rinse Slides (2xSSC Buffer) (Warm Slides to 95° C.)
6. Adjust Slide Volume, then Apply LCS™
7. Rinse Slides
8. Adjust Slide Volume, then Apply LCS™
9. Skip Application & Incubate for 4 minutes
10. Adjust Slide Volume, then Apply LCS™
11. Skip Application & Incubate for 4 minutes
12. Adjust Slide Volume, then Apply LCS™
13. Skip Application & Incubate for 4 minutes
14. Adjust Slide Volume, then Apply LCS™
15. Skip Application & Incubate for 4 minutes
16. Adjust Slide Volume, then Apply LCS™
17. Skip Application & Incubate for 4 minutes
18. Adjust Slide Volume, then Apply LCS™
19. Skip Application & Incubate for 4 minutes
20. Adjust Slide Volume, then Apply LCS™
21. Skip Application & Incubate for 4 minutes
22. Rinse Slides (2xSSC Buffer) (Warm Slides to 37° C.)
23. Adjust Slide Volume, then Apply LCS™
24. Skip Application & Incubate for 4 minutes
25. Rinse Slides (APK Wash)
26. Adjust Slide Volume, then Apply LCS™

Example 5

Automated "Exposing" and "Cell Conditioning" for Single Copy DNA Detection

Slides containing formalin fixed, paraffin embedded cell lines Caski (R96-1050A) and Siha (R96-96-C2), both generously provided by Dr. Raymond Tubbs, Cleveland Clinic Pathology Dept., Cleveland Ohio, were stained on Ventana target slides. Slides were dry loaded onto the instrument and the slide temperature was increased to 65° C. The Depar 30 protocol was run wherein the slides are rinsed with 2×SSC Buffer while at 65° C. then the heat is increased to 95° C. for about 40 minutes. The slides were then cooled to 37° C. and rinsed with APK wash. At this time the following in situ protocol was run:

In-Situ Protocol: Tubbs 1
  (Ventana APK Wash was used for all rinse steps)
  Protease Digestion: Protease 2, 4 minutes, 37 ° C.
  Inhibitor Step: Ventana Inhibitor from DAB kit 32 minutes 37° C.
  Probe: Enzo HPV Bio Probe 16/18
  Control Probe: Enzo HPV Bio Probe 6/11
  Denaturation: 95° C., 8 minutes
  Hybridization: 37° C., 64 minutes
  2 Stringency Washes 2×SSC, 60° C., 8 minutes each
  $3^{rd}$ Stringency Wash 2×SSC, 37° C., 4 minutes
  Probe Detection: Streptavidin HRPO (Dako GenPoint Cat. # K0620)
  Amplification: Biotinyl Tyramide (Dako GenPoint Cat. #K0620)
  Detection: Streptavidin HRPO (Dako GenPoint Cat. #K0620)or Streptavidin Alk Phos (Vector Cat. # SA5100)
  Chromogen DAB (Dako Gen Point Cat. # K0620) or
    Ventana NBT/BCIP (Kit P/N250-060) or
    Ventana Naphthol/Fast Red (Kit P/N250-030)

Example 6

Automated "Cell Conditioning" for Non-paraffin Embedded Samples

The protocol for DAB staining as described in Example 2 was used in this Example.

The cell conditioning steps for these antibodies was done after using a Cytyk 2000® instrument to make ThinPreps® of cell lines. The ThinPreps® were stained using antibodies to ER, PgR, Ki67, P53 on Ventana ES instruments, NexES instruments and a manual procedure (Cytyk, Inc.). A duplicate group of slides have been stained on the NexES Insitu module, allowing the cell conditioning steps to be performed by automation.

Although the example stated above is specific to the Cytyke® instrument and staining of the ThinPreps®, the experience is not limited to that mode of making cytological preps.

Example 7

"Cell Conditioning" of Frozen Biological Sample

Frozen tonsil blocks were prepared by cutting six sections from each block and placing the sample on microscope slides. Four slides from each block were placed on the Discovery™ in situ module and put through protocol Depar 10.

Slides are dry heated to 65° for 6 minutes then rinsed with 0.1M EDTA buffer pH 8. After rinsing, the slide is incubated at 65° for 20 minutes. Slides were then cooled to 37° C. and rinsed with APK Wash. Two slides from each block were left untreated as controls. Following the Depar 10 treatment two treated slides from each block and one untreated slide were stained for H & E as described in Example 1. Two treated slides from each block and one untreated from each block are stained for LCA. Run outcomes: for both the H & E and antibody staining there was no staining difference between the treated and untreated slides.

Example 8

Automated "Exposing" and "Cell Conditioning" for Immunohistochemistry

Various antibodies were assayed in the NexES Plus® (Ventana Medical Systems, Inc., Tuscon, Ariz.) automated environment according to the following protocol and flow chart:

Protocol:
(1) *** SelectEZPrep ***
(2) *** Start Timed Steps ***
(3) If deparaffinization is selected
(4) Warm slide to 75° C. and incubate for 4 minutes
(5) Adjust volume
(6) Apply LCS™
(7) Incubate for 8 minutes
(8) Rinse slide
(9) Adjust volume
(10) Apply LCS™
(11) Warm slide to 42° C. and incubate for 2 minutes
(12) If cell conditioning is selected
(13) If conditioner #1 is selected
(14) Rinse slide
(15) Adjust slide volume
(16) Apply LCS™
(17) Warm slide to 42° C. and incubate for 2 minutes
(18) Apply cell conditioning coverslip
(19) Warm slide to 100° C. and incubate for 2 minutes
(20) Apply cell conditioner #1
(21) Apply LCS™
(22) If standard is selected
(23) Incubate for 6 minutes
(24) Apply cell conditioner #1
(25) Apply LCS™
(26) Repeat (21)–(23) 9 times
(27) Warm slide to 42° C. and incubate for 2 minutes
(28) If mild is selected
(29) Incubate for 6 minutes
(30) Apply cell conditioner #1
(31) Apply LCS™
(32) Repeat (27)–(29) 4 times
(33) Warm slide to 42° C. and incubate for 2 minutes
(34) If extended is selected
(35) Incubate for 6 minutes
(36) Apply cell conditioner #1
(37) Apply LCS™
(38) Repeat (33)–(35) 14 times
(39) Warm slide to 42° C. and incubate for 2 minutes
(40) If conditioner #1 is not selected
(41) If conditioner #2 is selected
(42) Rinse slide
(43) Adjust slide volume

(44) Apply LCS™
(45) Warm slide to 42° C. and incubate for 2 minutes
(46) Apply cell conditioning coverslip
(47) Warm slide to 100° C. and incubate for 2 minutes
(48) Apply cell conditioner #2
(49) Apply LCS™
(50) If standard is selected
(51) Incubate for 6 minutes
(52) Apply cell conditioner #1
(53) Apply LCS™
(54) Repeat (49)–(51) 9 times
(55) Warm slide to 42° C. and incubate for 2 minutes
(56) If mild is selected
(57) Incubate for 6 minutes
(58) Apply cell conditioner #1
(59) Apply LCS™
(60) Repeat (55)–(57) 4 times
(61) Warm slide to 42° C. and incubate for 2 minutes
(62) If extended is selected
(63) Incubate for 6 minutes
(64) Apply cell conditioner #1
(65) Apply LCS™
(66) Repeat (61)–(63) 14 times Table I summarizes the results from automated immunohistochemistry assays performed on the NexES Plus (also known as the BENCHMARK™ IHC) using the automated deparaffinization and cell conditioning protocols described herein. The slides from the automated immunohistochemistry assays were compared to slides prepared using manual deparaffinization/cell conditioning protocols on a NexES instrument. Specific antibody slides were prepared in triplicate. Negative control slides were prepared singly. Slides from both assays were analyzed by persons skilled in the art and assigned ratings for specific staining intensity and non-specific background staining intensity. The ratings for all of the slides from the NexES Plus fully automated assays exceeded the ratings for the manually deparaffinized and cell conditioned NexES slides in both specific staining intensity and non-specific background intensity. Slides were analyzed and rated by a minimum of two independent persons skilled in the art and average staining intensities were determined. The column marked "Qualified Tissue" in Table 1 represents the standard control tissue used to standardize the antibody used on it. The standardized antibody is given a rating of 4.0. As can be seen in the column marked "Average Staining Intensity," most of the automated deparaffinized/cell conditioned slides met or exceeded those results.

TABLE 1

Antibody and Cell Conditioning Results

| Antibody | Clone | Qualified Tissue | Pretreatment | Incubation Time (minutes) | Negative Control | Average Staining Intensity | Negative Control |
|---|---|---|---|---|---|---|---|
| anti-PR | 1A6 | Endo11299#2 | 60 min. cell conditioning | 32 | NC Ig | 4 | 0 |
| anti-ER | 6F11 | UT31698V | 60 min. cell conditioning | 32 | NC Ig | 4 | 0 |
| anti-Pan Keratin | AE1, AE3, PCK26 | SK197A | 4 min. Protease 1 | 16 | NC Ig | 4 | 0 |
| anti-C-erbB-2 | CB11 | TMC197G | 60 min. cell conditioning | 32 | NC Ig | 4 | 0 |
| anti-S100 | polyclonal | p19 | None | 16 | Rbt NC | 4 | 0 |
| anti-CD20 | L26 | T1398H | None | 16 | NC Ig | 3.9 | 0 |
| anti-Vimentin | 3B4 | 245A | 8 min. Protease 2 | 16 | NC Ig | 4 | 0 |
| anti-LCA | RP2/18 | T31099B | None | 16 | NC Ig | 4 | 0 |
| anti-Melanosome | HMB45 | 97-715C | None | 16 | NC Ig | 4 | 0 |
| anti-CEA | TF-3H8-1 | CCA98157 | None | 16 | NC Ig | 4 | 0 |
| anti-CD45RO | A6 | T9810163 | None | 16 | NC Ig | 3.6 | 0 |
| anti-Chromogratin | LK2H10 | pN | None | 16 | NC Ig | 4 | 0 |
| anti-EMA | Mc5 | BRCA98139BC | None | 16 | NC Ig | 3.75 | 0 |
| anti-Kappa | Polyclonal | T4282 | 4 min. Protease 1 | 16 | Rbt NC | 4 | 0 |
| anti-Lambda | Polyclonal | 51099 | 4 min. Protease 1 | 16 | Rbt NC | 4 | 0 |
| anti-CD15 | MMA | K121698 | None | 16 | NC Ig | 4 | 0 |
| anti-Desmin | DE-R-11 | SI173BC | 16 min Protease 2 | 16 | NC Ig | 4 | 0 |
| anti-Muscle Actin | HUC1-1 | DIA8699A | None | 16 | NC Ig | 4 | 0 |
| anti-PSA | Polyclonal | 271A | None | 16 | Rbt NC | 4 | 0 |
| anti-Ki67 | MM1 | P92-3622 | 60 min. cell conditioning | 16 | NC Ig | 3.9 | 0 |
| anti-p53 | bp-53-11 | EV246B | 60 min. cell conditioning | 16 | NC Ig | 4 | 0 |
| anti-Keratin | 5D3 | L103CB | 8 min Protease 1 | 16 | NC Ig | 4 | 0 |
| anti-NSE | BBS/NC/VI-H14 | #2 | None | 16 | NC Ig | 3.9 | 0 |
| anti-bcl-2 | bcl-2/100/D5 | Block6 | 60 min. cell conditioning | 32 | NC Ig | 4 | 0 |
| anti-CD30 | 1G12 | HodgkinsI912696C | 60 min. cell conditioning | 16 | NC Ig | 3.75 | 0 |
| anti-CD43 | L60 | TI1698H | None | 16 | NC Ig | 3.75 | 0 |
| anti-GFAP | Polyclonal | CBR9872E | None | 16 | Rbt NC | 4 | 0 |
| anti-Synaptophysin | 27G12 | 406A | ND | 16 | ND | 4 | 0 |

NOTE: In Table 1, ND stands for No Data.

(67) Warm slide to 42° C. and incubate for 2 minutes
(68) Rinse slide
(69) Adjust slide volume
(70) Apply LCS™
(71) Disable slide heater
(72) *** Select Reaction Buffer ***

The primary antibodies (available from Ventana Medical Systems, Inc., Tuscon, Ariz.) referred to in Table 1 (above) are described below, in alphabetical order:

anti-bcl-2:

Clone bcl-2/100/D5 is a monoclonal antibody used to detect bcl-2, which is an inhibitor of apoptosis. This antibody may be an aid to distinguish between reactive and neoplastic follicular proliferation. Control: Tonsil. (VMSI # 760-2693)

anti-C-erbB-2 (HER2/neu):
Clone CB11 is a monoclonal antibody to c-erb-B2, which is localized on the cell membrane, and occasionally, in the cytoplasm of some neoplastic cells. (VMSI # 760-2994)

anti-CD 15:
Clone MMA is a monoclonal antibody used to aid in the identification of cells of the granulocytic lineage and/or Reed-Stemberg differentiation. Control: Hodgkin's Lymphoma. (VMSI #760-2504)

anti-CD20:
Clone L26 is a monoclonal antibody used to aid in the identification of cells of the B lymphocytic lineage. Contol: Tonsil. (VMSI #760-2531/760-2137)

anti-CD43:
Clone L60 is a monoclonal antibody that specifically binds to antigens located in the plasma membrane of normal granulocytes and T lymphocytes. Control: Tonsil. (VMSI # 760-2511)

anti-CD45RA:
Clone X148 is a monoclonal antibody that specifically binds to antigens located in the plasma membrane of normal B lymphocytes and a subset of T lymphocytes. Control: Tonsil. (VMSI # 76-2510)

anti-CD45RO:
Clone A6 is a monoclonal antibody that binds to the plasma membrane of cells of the T lineage and a subset of B-cells. Control: Tonsil. (VMSI # 760-2563)

anti-CEA:
Clone TF-3H8-1 specifically binds to antigens located in the plasma membrane and cytoplasmic regions of mucosal epithelial cells. Control: Colon Carcinoma. (VMSI # 760-2507/760-2141)

anti-Chromogranin:
Clone LK2H10 is a monoclonal antibody that binds the chromogranin protein located in the secretory granules of normal and neoplastic neuroendocrine cells. Control: Pancreas. (VMSI # 760-2519/760-2140)

anti-Desmin:
Clone DE-R-11 is a monoclonal antibody used to aid in the identification of cells of the myocytic lineage. Desmin is an intermediate filament found in mature smooth, striated and cardiac muscle. Control: Vas Deferens. (VMSI # 760-2513)

anti-EGFR:
Clone 31G7 is directed against a transmembrane glycoprotein present on a variety of cells. (VMSI # 760-2548)

anti-EMA:
Clone Mc5 is a monoclonal antibody used to aid in the identification of cells of epithelial lineage. EMA is of value in distinguishing both large-cell anaplastic carcinoma from diffuse histiocytic lymphoma, and small-cell anaplastic carcinoma from well and poorly differentiated lymphocytic lymphomas. Control: Carcinoma. (VMSI # 760-2508)

anti-ER:
Clone 6F11 is a monoclonal antibody used to detect the presence of estrogen receptor. (VMSI # 760-2596/760-2132)
Clone CC4-5 is a monoclonal antibody also used to detect the presence of estrogen receptor. (VMSI # 760-2546/760-2138)

anti-GFAP:
GFAP polyclonal antibody is directed against glial fibrillary acidic protein present in the cytoplasm of most human astrocytes and ependymal cells. This reagent may be used to aid in the identification of cells of the glial lineage. Control: Brain. (VMSI # 760-2516)

anti-Kappa:
Kappa light chains are expressed by cells of the B-cell lineage. Light chain production by lymphoid cells is genetically restricted such that the immunoglobulin molecules produced by an individual cell will only contain a single light chain class. This clonal restriction may be used to indicate the polyclonal or monoclonal nature of B-cell and plasma cell populations. Control: Plasmacytoma. (VMSI # 760-2514)

anti-Keratin:
Clone 5D3 is a monoclonal antibody raised against human epidermal keratins. This antibody may be used to aid in the identification of cells of the epithelial lineage. This antibody reacts with cytokeratins 8 and 18. Control: Carcinoma. (VMSI # 760-2501)

Clone AE1 is a monoclonal antibody raised against human epidermal keratins. This antibody may be used to aid in the identification of cells of the ductal epithelial lineage. AE1 reacts with cytokeratins 10, 13, 14, 15 and 19. Control: Liver. (VMSI # 760-2521)

anti-Pan Keratin:
Pan Keratin is a cocktail of monoclonal antibody clones AE1/AE3/PCK26 used to aid in the identification of cells of the epithelial lineage. This antibody cocktail reacts with all cytokeratins except 9, 11 and 12. Control: Skin. (VMSI # 760-2595/760-2135)

anti-Ki67:
Clone MM1 is a monoclonal antibody that specifically binds to nuclear antigens associated with cell proliferation that are present throughout the active cell cycle (G1, S, G2 and M phases), but absent in resting (G0 phase) cells. This reagent may be used to aid in the identification of proliferating cells. Control: Tonsil. (VMSI # 760-2520)

anti-Lambda:
Lambda light chains are expressed by cells of the B-cell lineage. Light chain production by lymphoid cells is genetically restricted, such that the immunoglobulin molecules produced by an individual cell will only contain a single light chain class. This clonal restriction may be an aid to indicate the polyclonal or monoclonal nature of B-cell and plasma cell populations. Control: Plasmacytoma. (VMSI # 760-2515)

anti-LCA:
Clone RP2/18 is a is a monoclonal antibody used to aid in the identification of cells of lymphocytic descent. This antibody specifically binds to antigens located predominantly in the plasma membrane and cytoplasmic rim of lymphocytes with variable reactivity to monocytes/histocytes and polymorphs. Control: Lymphoma. (VMSI # 760-2505/760-2136)

anti-Melanosome:
Clone HMB45 monoclonal antibody is used to aid in the identification of cells of the melanocytic lineage. It reacts with an antigen expressed in abnormal melanocytes and melanoma cells. Control: Melanoma. (VMSI # 760-2518/760-2139)

anti-Muscle Actin:
Clone HUC1-1 is a monoclonal antibody used to aid in the identification of cells of myocytic descent. Muscle actin is expressed in cells of the striated, smooth and cardiac muscle lineage. Control: Ileum. (VMSI # 760-2502)

anti-NSE:
Clone BBS/NC/VI-H14 is a monoclonal antibody that reacts with an antigen that may be expressed in the cytoplasm of neurons, neuro-endocrine cells, endocrine tumors, carcinoids and Merkel cell tumors. Control: Pancreas. (VMSI # 76-2517)

anti-p53:
Clone Bp-53-11 is a monoclonal antibody directed against the p53 protein. This reagent may be used to aid in the identification of abnormally proliferating cells in neoplastic cell populations. Control: Carcinoma. (VMSI # 760-2540)

anti-PCNA:
Clone PC10 is a monoclonal antibody that may be used to aid in the identification of proliferating cells in various cell populations. The PCNA antigen is expressed in all proliferating cells in the G1, S, G2 and M phases. Control: Tonsil. (VMSI # 760-2503)

anti-PSA:
PSA polyclonal antibody reacts with the secretory protein expressed in the cytoplasm of prostate epithelial cells. Control: Prostate. (VMSI # 760-2506)

anti-PSAP:
Clone PASE/4LJ is a monoclonal antibody used to aid in the identification of cells of the prostate lineage. PSAP specifically binds to antigens located in the cytoplasmic regions of the normal prostate epithelial cells. Control: Prostate. (VMSI # 760-2509)

anti-PR:
Clone 1A6 is a monoclonal antibody used to aid in the identification of the progesterone receptor in human tissue. (VMSI # 760-2547/760-2133)

anti-S100:
S100 polyclonal antibody is used to aid in the identification of cells of normal and abnormal neuro-endocrine descent. Control: Skin. (VMSI # 760-2523/760-2133)

anti-Vimentin:
Clone 3B4 is used to aid in the identification of cells of mesenchymal origin. Control: Vas Deferens. (VMSI # 760-2512/760-2134)

Negative Control:
Polyclonal serum applied to negative tissue controls as part of quality control procedures for polyclonal antibodies. (VMSI # 760-1023)

Negative Control Ig:
Clone MOPC-21 is applied to negative tissue controls as part of quality control procedures for monoclonal antibodies. (VMSI # 760-2014)

Example 9

Automated "Cell Conditioning" with or without "Exposing" for Immunohistochemistry (IHC), Immunocytochemistry (ICC) or In situ Hybribidization (ISH)

The CC2 solution may be used on automated immunohistochemical, immunocytochemical or in situ hybridization instruments (e.g., BenchMark™ ISH, Ventana Medical Systems, Inc., Tucson, Ariz.; BenchMark™ IHC, Ventana Medical Systems, Inc., Tucson, Ariz.; etc.) with reagents designed to detect the c-erb2/HER-2/neu gene or protein(s) expressed therefrom (e.g., INFORM® HER-2/neu DNA test, Ventana Medical Systems, Inc., Tucson, Ariz.; PATHWAY™ HER-2/neu (CB11) protein test, Ventana Medical Systems, Inc., Tucson, Ariz.; etc.).

For an ISH assay, the CC2 solution may preferably be used in an automated pretreatment step following deparaffinization with the CC2 solution applied to the tissue at about 90° C. for about 10 minutes prior to application of the DNA probe. The heat treatment in conjunction with the CC2 solution allows the genomic DNA to become better suited for binding with the c-erb2/HER-2/neu DNA probe.

For an IHC assay, the CC2 solution may preferably be used in an automated cell conditioning step following deparaffinization with the CC2 solution applied to the tissue at about 95° C. for about 30 minutes. The high temperature in conjunction with the CC2 solution allows the c-erb2/HER-2/neu protein (antigen or epitope) to become better suited for binding with the anti-c-erb2/HER-2/neu antibody.

These are representative contexts in which the CC2 solution is preferably used. The CC2 solution is also useful in many other assays, techniques, protocols or procedures designed to detect the presence or absence of targeted DNA or protein molecules under consideration.

Example 10

Deparaffinization by Contacting a Sample Using a Heated Fluid

Figure 8:
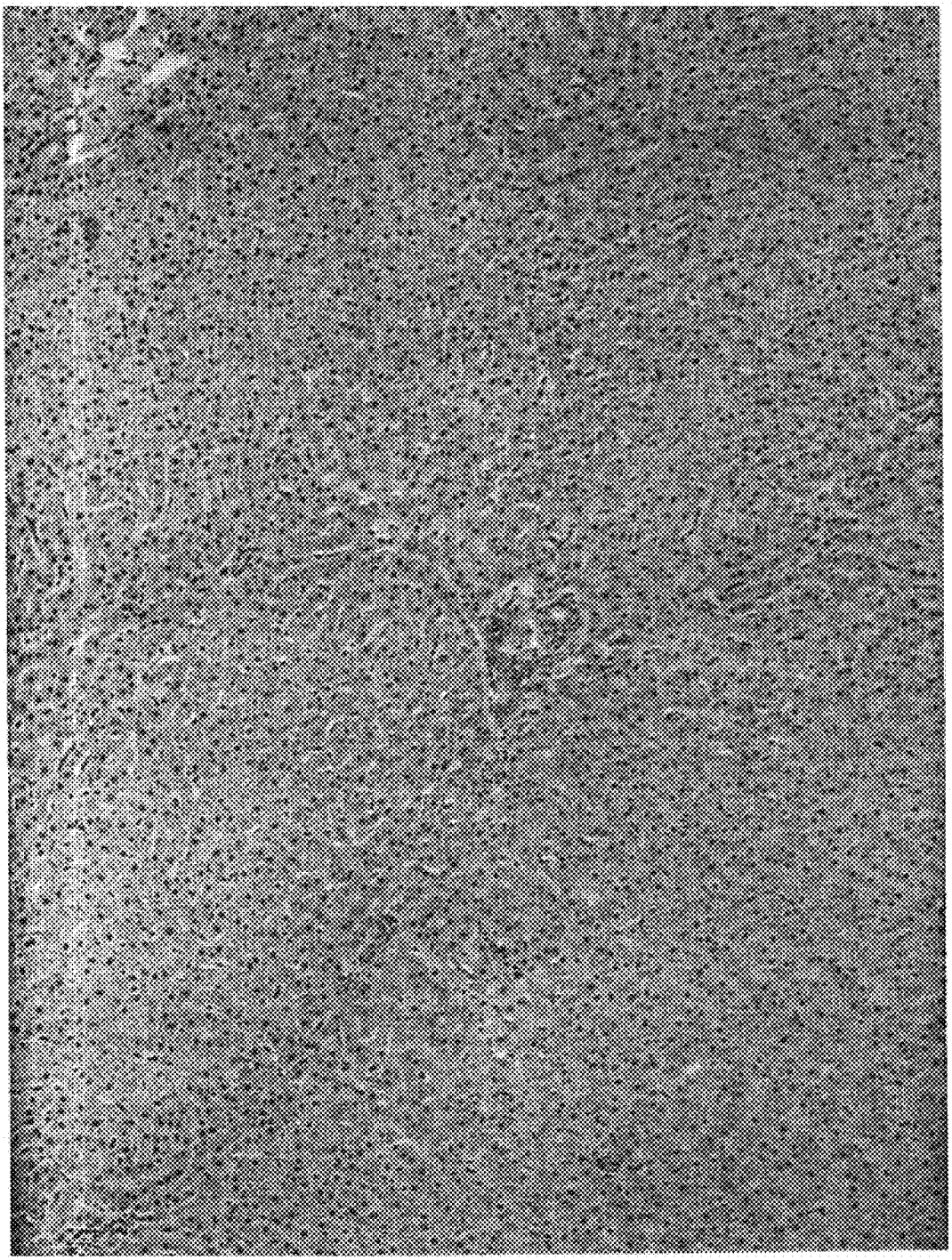
FIG. 8 is a picture of a standard H&E stain performed on a bovine liver section that was deparaffinized according to one embodiment of the invention.

Using the alternative embodiment disclosed herein, a standard H&E stain was performed on a bovine liver section (FIG. 8). The sample slide was supported on a 20-slide tray modified so that hot EZ Prep™ (Ventana) could be applied for a predetermined time period (in one embodiment, at least 5 minutes).

A small recirculator pump (Flojet Model No. 4300-042, Foothills Ranch, Calif.) was used to dispense a high volume (1200 ml/min) of heated fluid (in one embodiment, 65–70° C. EZ Prep) on the slide for 5 minutes. A standard immersion heater was used to raise and maintain the temperature of the buffer.

The deparaffinized slides were stained using standard H&E protocols. Controls were also run that had been deparaffinized using either traditional solvent methods or automated methods on a Discovery™ instrument (Ventana). After comparing all three methods, it was concluded that the slides undergoing recirculated hot EZ Prep had produced the best results.

As seen in FIG. 8, after staining the tissue, no signs of paraffin could be found, and tissue morphology did not seem to be altered. Several additional slides were processed using the same method with similar results. Experiments were conducted to determine what effect flow rates had on results. Preliminary data suggested that when flow rates of the fluid were lowered to below 400 ml/min, staining was not as good.

From the foregoing detailed description, it will be appreciated that numerous changes and modifications can be made to the aspects of the invention without departure from the true spirit and scope of the invention. This true spirit and scope of the invention is defined by the appended claims, to be interpreted in light of the foregoing specification.

We claim:

1. An automated method of removing embedding media from a biological sample on a microscope slide, the method comprising the sequential steps of:
   a) separately heating a fluid, the fluid being immiscible with the embedding media; and
   b) contacting said biological sample with said heated immiscible fluid thereby heating the embedding media sufficient to separate the embedding media from the biological sample.

2. The method of claim 1, wherein the step of heating the immiscible fluid heats the immiscible fluid to a temperature above a melting point of the embedding media.

3. The method of claim 2, wherein said heating step requires the temperature of said immiscible fluid to be at least about 65 degrees centigrade.

4. The method of claim 3, wherein said embedding media is paraffin or paraffin-based.

5. The method of claim 2, wherein contacting the biological sample is carried out by dispensing said immiscible fluid onto the biological sample and maintaining the temperature of the immiscible fluid above the melting point of the embedding media.

6. The method of claim 5, wherein maintaining the temperature is effected by recirculating said immiscible fluid.

7. The method of claim 2, further comprising the step of heating the biological sample and the embedding media.

8. The method of claim 7, wherein the step of heating the biological sample and the embedding media includes heating the biological sample and the embedding media above a melting point of the embedding media.

9. The method of claim 1, wherein contacting the biological sample includes rinsing the biological sample with said heated immiscible fluid.

10. The method of claim 9, wherein the step of rinsing the biological sample with said heated immiscible fluid comprises rising the biological sample with a continuous stream of the heated immiscible fluid.

11. The method of claim 1, further comprising the step of heating the biological sample and the embedding media.

12. The method of claim 11, wherein the step of heating the biological sample and the embedding media includes heating the biological sample and the embedding media above a melting point of the embedding media.

13. The method of claim 1, wherein separating the embedding media from the biological sample includes causing the embedding media to float on the immiscible fluid so as to be removed.

14. The method of claim 1, wherein the immiscible fluid comprises water.

15. The method of claim 1, wherein the immiscible fluid is selected from the group consisting of de-ionized water, citrate buffer (pH 6.0–8.0), Tris-HCl buffer (pH 6–10), phosphate buffer (pH 6.0–8.0), SSC buffer, acidic buffers or solutions (pH 1–6.9), basic buffers or solutions (pH 7.1–14), mineral oil, Norpar, canola oil, and PAG oil.

16. The method of claim 1, wherein the immiscible fluid contains ionic or non-ionic surfactants.

\* \* \* \* \*